(12) United States Patent
Starker et al.

(10) Patent No.: US 9,204,979 B2
(45) Date of Patent: Dec. 8, 2015

(54) ARTIFICIAL ANKLE, ARTIFICIAL FOOT AND ARTIFICIAL LEG

(75) Inventors: Felix Starker, Stuttgart (DE); Urs Schneider, Stuttgart (DE); Andrew H. Hansen, Apple Valley, MN (US); Dudley S. Childress, Wilmette, IL (US); Joachim Pauli, Naunhof (DE); Carsten Pauli, Leipzig (DE); Nancy Childress, legal representative, Wilmette, IL (US)

(73) Assignees: FALZ & KANNENBERG GMBH & CO. KG, Brandis (DE); NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 13/979,249

(22) PCT Filed: Jan. 11, 2011

(86) PCT No.: PCT/EP2011/000079
§ 371 (c)(1),
(2), (4) Date: Nov. 19, 2013

(87) PCT Pub. No.: WO2012/095115
PCT Pub. Date: Jul. 19, 2012

(65) Prior Publication Data
US 2014/0074255 A1    Mar. 13, 2014

(51) Int. Cl.
*A61F 2/66* (2006.01)
*A61F 2/68* (2006.01)
*A61F 2/50* (2006.01)
*A61F 2/60* (2006.01)
*A61F 2/74* (2006.01)

(52) U.S. Cl.
CPC ............. *A61F 2/6607* (2013.01); *A61F 2/68* (2013.01); *A61F 2002/5006* (2013.01); *A61F 2002/607* (2013.01); *A61F 2002/6818* (2013.01); *A61F 2002/6854* (2013.01); *A61F 2002/744* (2013.01); *A61F 2002/745* (2013.01); *A61F 2002/748* (2013.01)

(58) Field of Classification Search
USPC .......................................... 623/26, 44, 47, 50
See application file for complete search history.

(56) References Cited

U.S. PATENT DOCUMENTS

| | | |
|---|---|---|
| 2,843,853 A | 7/1958 | Mauch |
| 2006/0224248 A1 | 10/2006 | Lang |
| 2006/0235544 A1 | 10/2006 | Iversen et al. |
| 2008/0255670 A1 | 10/2008 | Boiten et al. |
| 2008/0300692 A1 | 12/2008 | Moser et al. |

FOREIGN PATENT DOCUMENTS

| | | |
|---|---|---|
| EP | 0654254 A1 | 5/1995 |
| WO | WO 2009/015473 A1 | 5/2009 |

OTHER PUBLICATIONS

"A preliminary clinical evaluation of the Mauch hydraulic foot-ankle system", Sowell, pp. 87-91, 1981.*

* cited by examiner

*Primary Examiner* — Bruce E Snow
(74) *Attorney, Agent, or Firm* — Jacobson Holman, PLLC.

(57) ABSTRACT

The present invention relates in the field of orthopedics to an artificial ankle which imitates the natural human gait in a proper way, thereby enabling its user to walk not only in a plane environment but also uphill and downhill without any unpleasant effects. The present invention further relates to an artificial foot and an artificial leg containing said artificial ankle.

13 Claims, 29 Drawing Sheets

Figure 2:
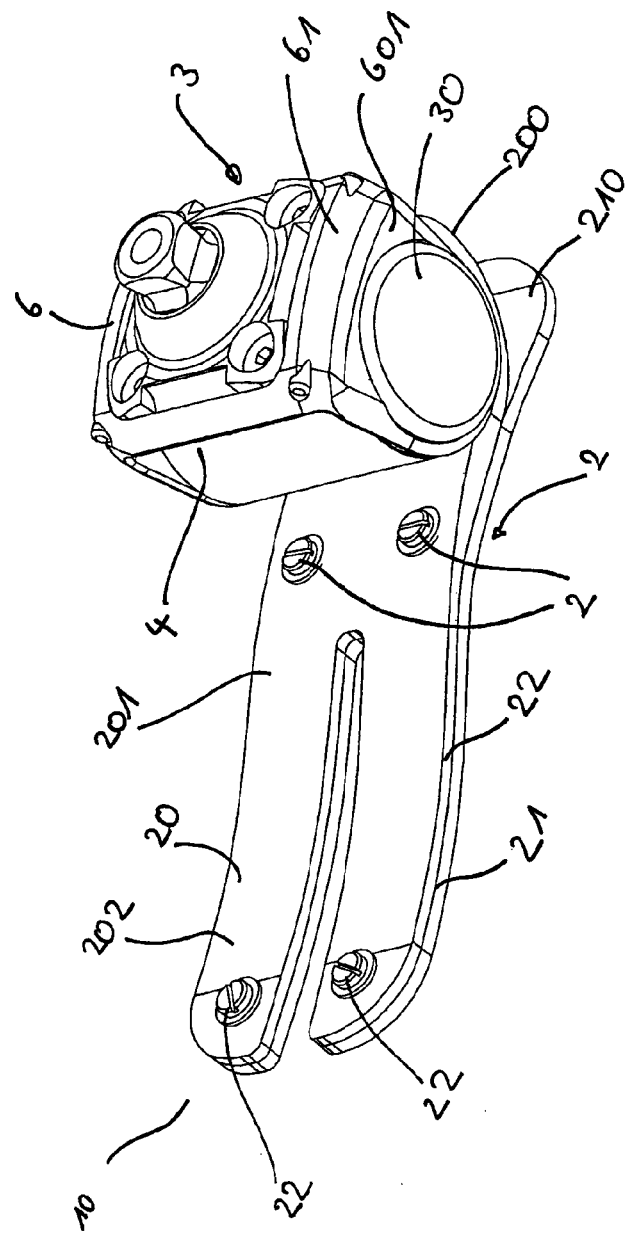

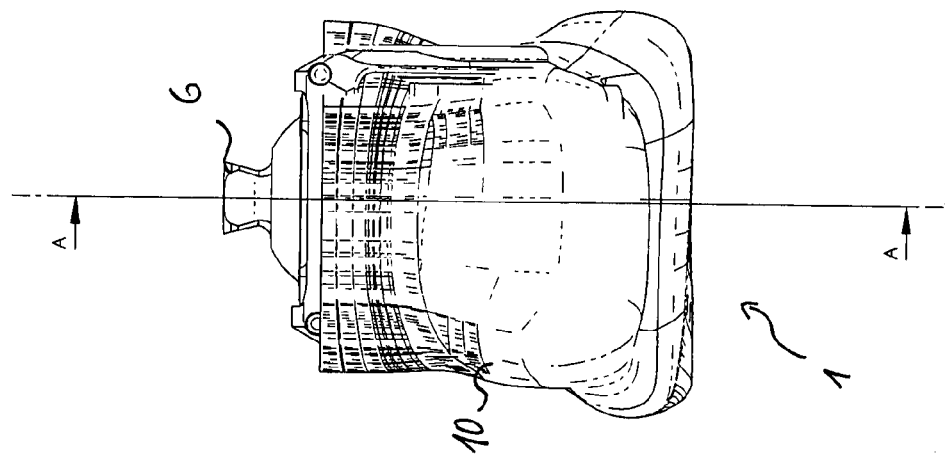
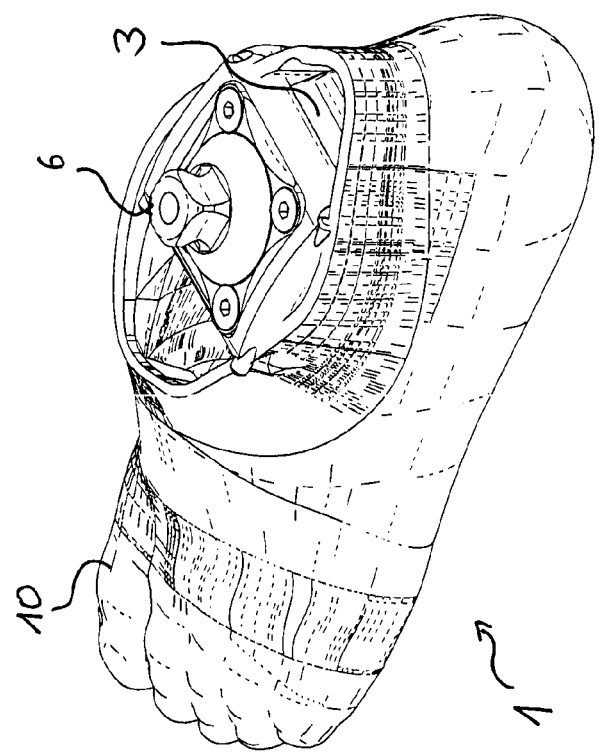
Figure 1A
Figure 1B

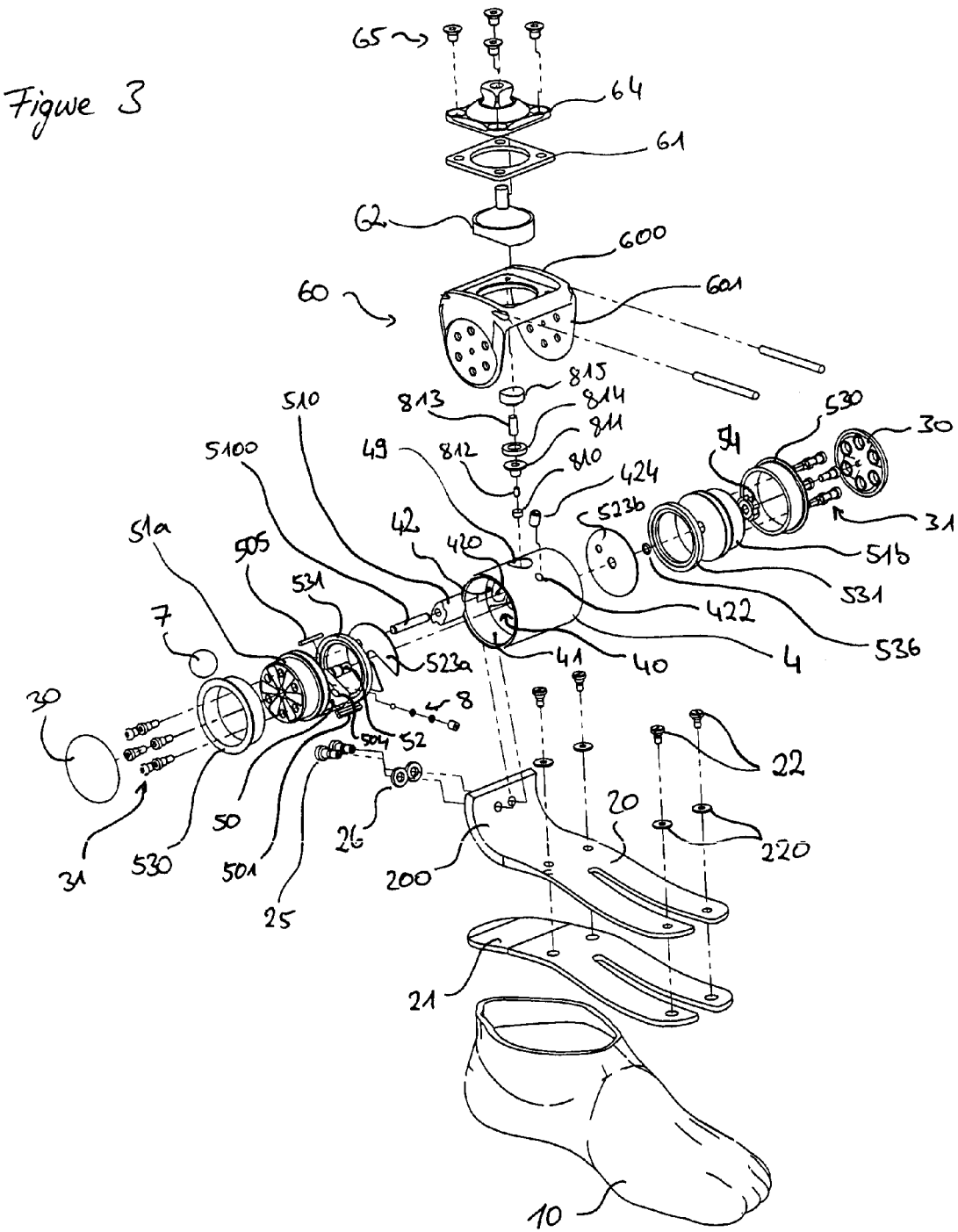

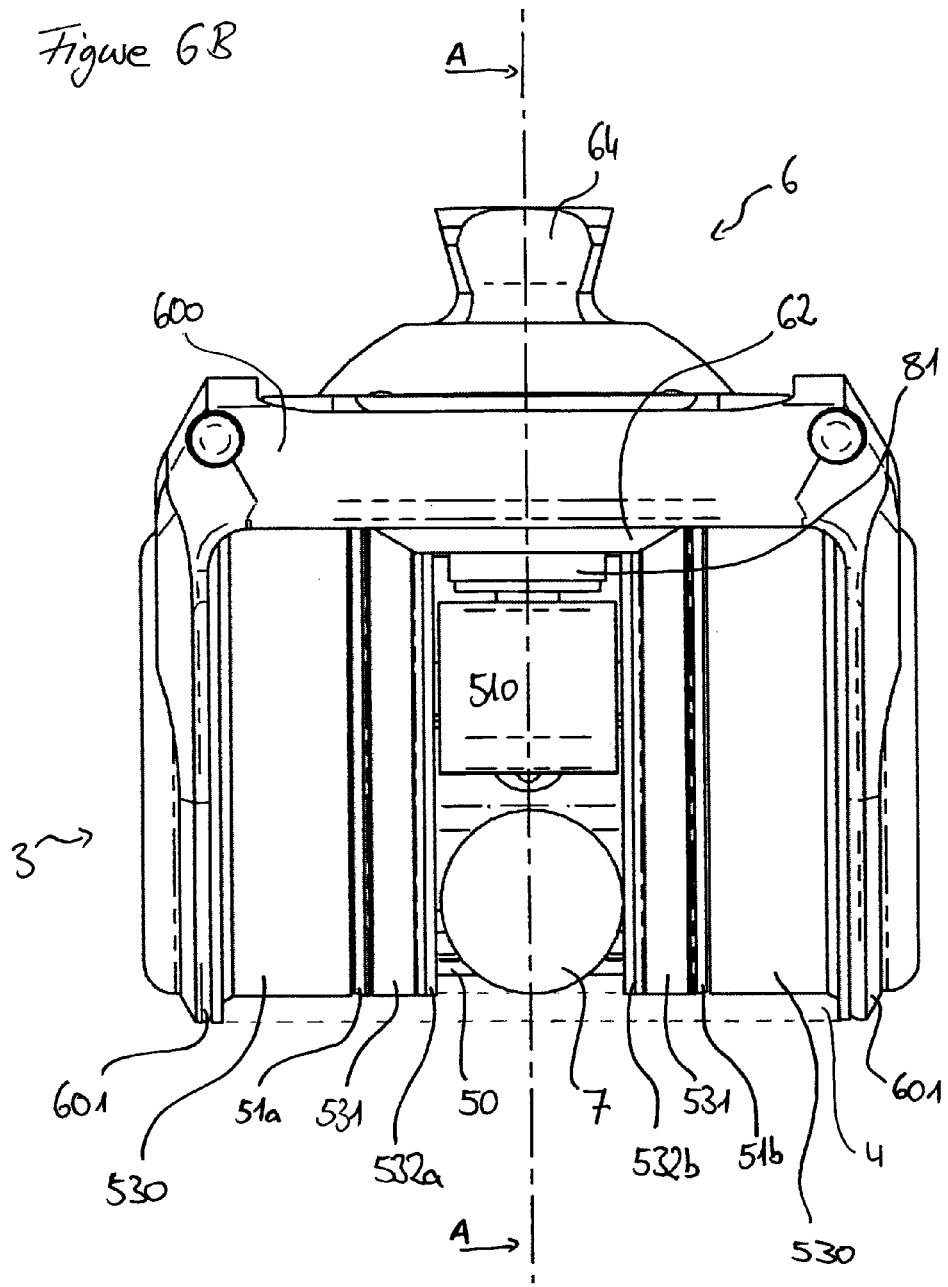

A-A

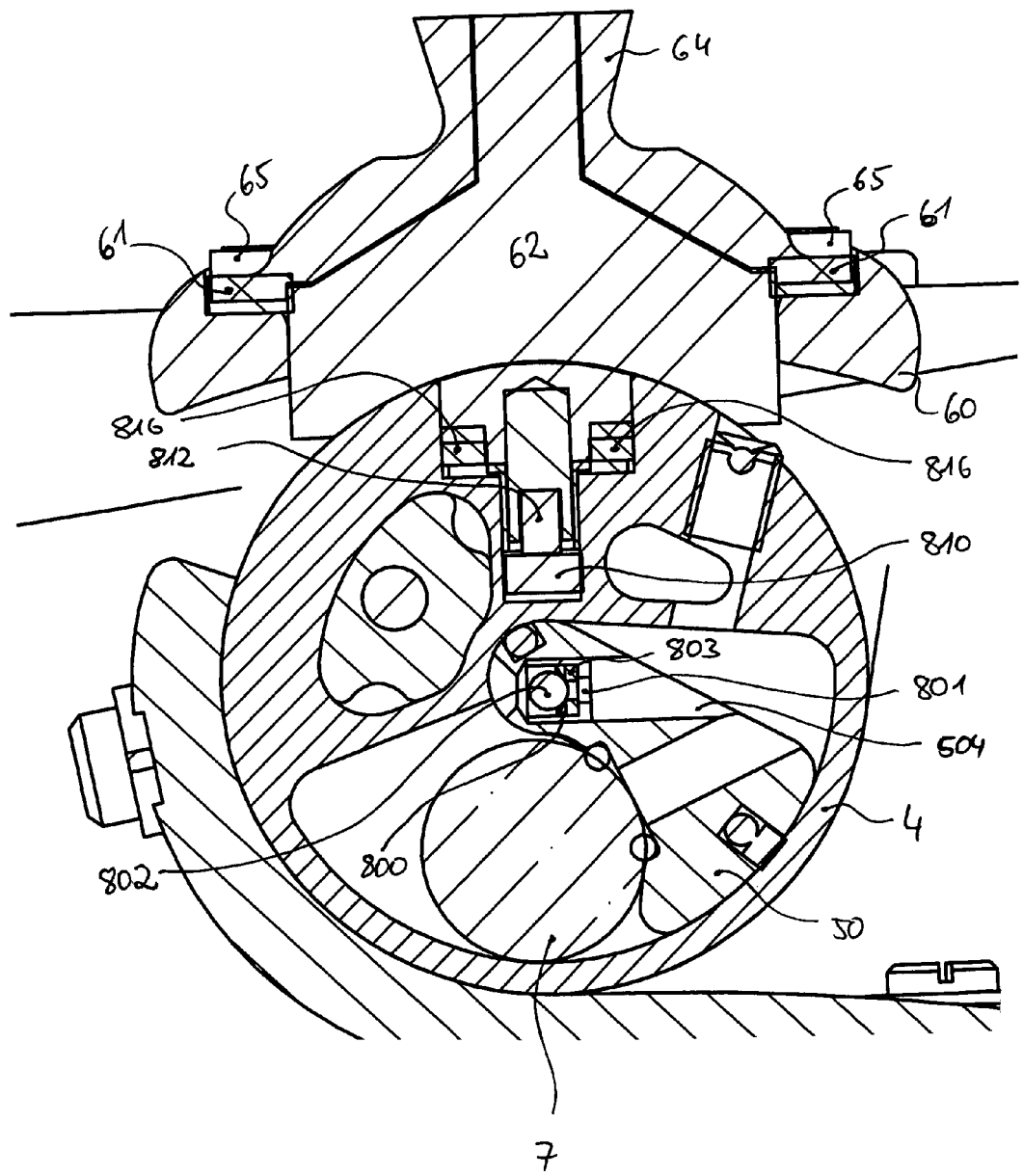

H-H

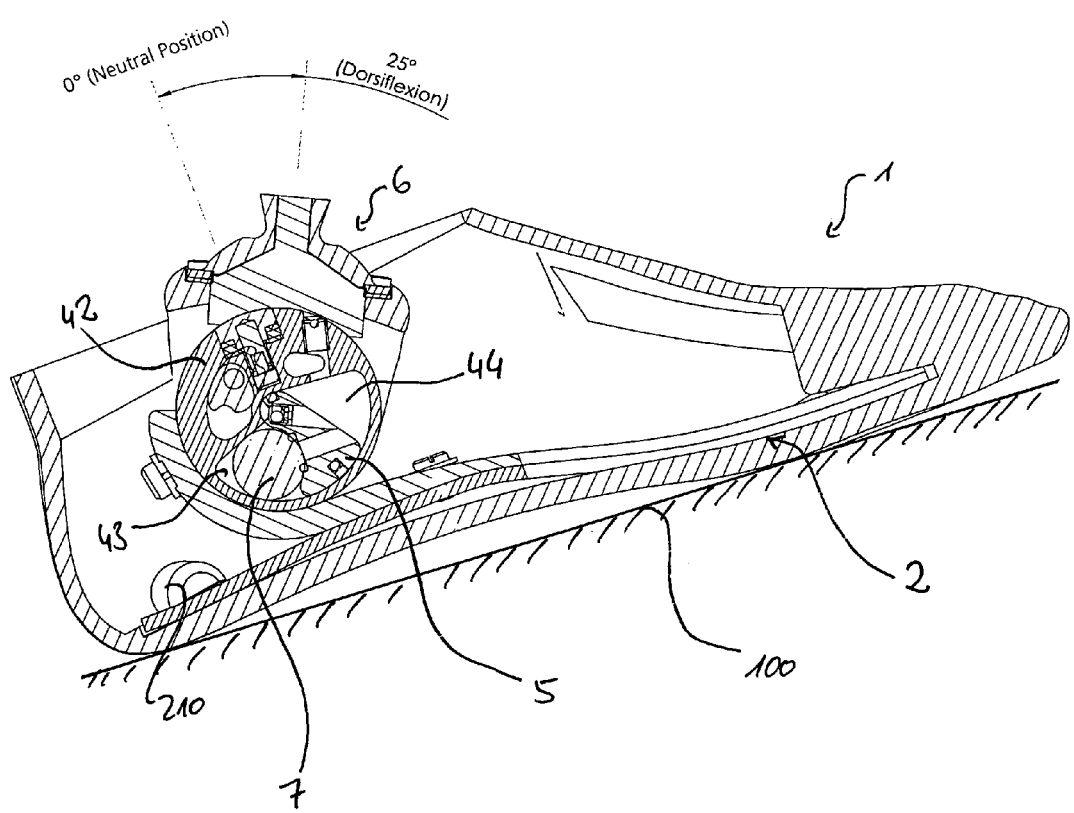

ARTIFICIAL ANKLE, ARTIFICIAL FOOT AND ARTIFICIAL LEG

This is a national stage of PCT/EP11/000079 filed Jan. 11, 2011 and published in English, hereby incorporated by reference.

The present invention relates in the field of orthopedics to an artificial ankle which imitates the natural human gait in a proper way, thereby enabling its user to walk not only in a plane environment but also uphill and downhill without any unpleasant effects. The present invention further relates to an artificial foot and an artificial leg containing said artificial ankle.

From the state of the art, several types of artificial ankles are known. Said artificial ankles which are preferably based on mechanical techniques are configured such, that their course of motion during walking is simplified compared to the natural human gait and therefore causes difficulties and dangers for the user. In order to avoid said simplification, very difficult and therefore expensive solutions were proposed.

Therefore, several attempts were made to construct an improved artificial ankle based not only on mechanical but also on hydraulic ideas.

A broad overview over artificial ankles known from the state of the art is given by the patent application publication US 2008/0300692 A1.

A further example for a hydraulic ankle imitating the natural human gait in a good way is described in U.S. Pat. No. 2,843,853 by Hans A. Mauch. He proposes an artificial ankle, containing a foot and a shank forming a cavity in their connecting region. Said cavity contains a hydraulic device for avoiding motion between the foot and the shank at time of load.

Said hydraulic device has a housing within which a piston arranged parallel to the shank pivots around a rotational axis over a convex shaped surface. The piston has a vane shaped end that separates the inside of the housing into two chambers that are filled with hydraulic fluid. The housing has a flexible cover to prevent fluid leakage. At the vane shaped end of the piston is a bore, the so-called control channel that connects both separated hydraulic chambers.

At the rear warded hydraulic chamber is a ball in a cage. The ball always seeks for the minimum of energy and hence rolls to the lowest point in the cage, so that the ball detects the position of the housing relative to the surrounding environment. When the ball contacts the piston, the control channel is closed, preventing fluid to intersect between both hydraulic chambers. This feature allows the hydraulic joint to provide soft spring impedance, when the ball is not blocking the control channel and high spring impedance when the ball is blocking the control channel.

Even though the course of motion of said artificial ankle is well adapted to the natural human gait, the construction disclosed by Mauch has the disadvantage that the cover of the housing of the hydraulic device is not stably fluid tight so that the hydraulic fluid leaks. Furthermore, the specific design with a molded housing proposed by Mauch shows several internal areas for possible leakage.

Based on this construction of an artificial ankle of the state of the art, it is the object of the present invention to provide an artificial ankle which overcomes the problem of leakage, which can be easily constructed and which can be produced at low cost.

This object is solved by the artificial ankle according to claim 1, the artificial foot according to claim 11 and the artificial leg according to claim 13. Advantageous improvements of the artificial ankle and the artificial foot are described by the corresponding dependent claims.

According to the present invention, an artificial ankle comprises a housing containing a hollow body, a vane type piston arranged in the hollow body, gravity controlled means and attachment means. The hollow body of the housing is formed for retaining or comprising a hydraulic fluid within the hollow body. Said hollow body has an inner face, wherein said inner face or at least a part thereof has a cylindrical surface area having a rotational axis.

The vane type piston arranged within the hollow body and having axial ends is configured to pivot about the rotational axis of the cylindrical surface area in a sealing manner with said cylindrical surface area, wherein said sealing between the piston and said cylindrical surface area separates the hollow body on both sides of the vane type piston in a fluid tight manner. The vane type piston thereby has at least one aperture to allow fluid to move between both sides of the piston which can be opened or closed by the gravity controlled means.

The vane type piston contains at least one supporting element at one of its axial ends, preferably at each of its both axial ends, the supporting element being connected in a fluid tight sealing manner with the hollow body in order to retain the hydraulic fluid within the hollow body.

The hollow body is closed on at least one of its face sides, which are preferably perpendicular to its cylindrical surface area, preferably on both its face sides, by the at least one supporting element formed to fluid tightly seal the space (hollow body) enclosed by the housing and the supporting element in order to retain the hydraulic fluid within the hollow body.

The attachment means for attaching a shank to the artificial ankle is fixed to the piston, in particular to at least one axial ends or the supporting element of the piston, preferably to both axial ends and/or the supporting elements at both axial ends, outside of the hollow body.

According to the present invention, the gravity controlled means seeks for the minimum of energy and hence moves to the lowest point on the cylindrical surface area of the housing. This means that the gravity controlled means inside the assembly detects the position of the housing relative to the surrounding environment. The vane type piston is configured so that the gravity controlled means contacts the piston to close said aperture of the piston when the attachment means is in a position so as to fix the shank in a substantially vertical position.

The present invention thus provides an artificial ankle which does not require a flexible cover with high leakage probability. In the ankle of the present invention, the flexible cover of the state of the art is avoided by attaching the shank or the attachment means laterally to the piston, the hollow body being formed by components, preferably rigid components, rotatable relative to each other.

The artificial ankle of the present invention is configured such that the hollow body provided by the housing and the at least one supporting element are fluid tightly sealed. As the housing and the piston are rotatable relative to each other, the junction surfaces of the housing and the at least one supporting element, which advantageously has circular cross section, are preferably cylindrically shaped. The junction can therefore be easily sealed by using a suitable sealing, in particular a standard ring sealing, e.g. a hydraulic seal ring or an O-ring. Due to the form of said junction surfaces an effective sealing of the hollow body is achieved and the problem of leakage is successfully avoided.

The hollow body of the housing can be formed open at, e.g. without, one or both of its face sides. In such a case, the at least one supporting element of the vane type piston may have the form of a side face fully covering said open side of the hollow body.

Furthermore, at least one of the side faces of the hollow body can be partially covered by a side wall, which is fixed to the housing in a removable manner, e.g. by using one or more screws and if necessary a seal, in particular a ring seal, or in a permanent manner by merging it, preferably soldering it, to the housing. Said side wall may have an opening in the region of the rotational axis, into which the supporting element can be placed in a sealing manner. Alternatively said side wall can be formed in one piece with the housing.

Furthermore, in case, that the attachment means are fixed only to one axial end or supporting element, the side face opposite to the axial end in connection with the attachment means, can be fully covered by a continuous side wall, fixed to the housing in a removable or permanent manner or formed integrally, e.g. in one piece, with the housing.

The vane type piston preferably has a vane element rotating around the rotational axis, which can be formed like a rectangular plate. More preferably the rectangular plate has a bar at its portion adjacent to the cylindrical surface area resulting in a T-shaped or L-shaped cross section. Furthermore, the opposite edge of the plate opposite to the portion provided with the bar and to be arranged in the vicinity of the rotational axis may be rounded off.

The at least one aperture of the vane-type piston may be a simple throughhole or a two-way flow control for separately controlling dorsiflexion (forward rotation) and plantarflexion (backward rotation). In order to control the flow velocity through the at least one aperture, a means for generating a turbulent flow may be displaced in and/or in front of said aperture.

The sealing between the piston and the cylindrical surface area may be achieved by forming the contacting surfaces between the piston and the housing as flat as possible, so that a motion can be realized even if the two components are in direct contact. Furthermore or alternatively, the piston may be provided with a suitable seal on its surfaces facing the housing. Preferably, such seal is disposed in a groove formed at least on one of the surfaces of the piston facing the housing.

The gravity controlled means may have a cylindrical or spherical surface for freely rolling on the cylindrical surface area of the hollow body on one side of the vane type piston. Said gravity controlled means may be a ball or a cylinder. Preferably, the diameter of the ball corresponds to the width of the hollow body between the side faces of the hollow body, such that a ball cage for guiding the ball to assure the ball under certain conditions to be in a correct position to close the control port (aperture) inside the piston is not necessary.

Said gravity controlled means changes its position relative to the cylindrical surface area as consequence of a movement of the artificial ankle such that the gravity controlled means is placed at the lowest point of the cylindrical surface area. As soon as the attachment means is in a position so as to fix the shank in a substantially vertical position, the piston is positioned such that the gravity controlled means closes the aperture. In order to make sure, that the aperture is closed in a fluid tight manner, the aperture may be surrounded by a ring seal on the side directed towards the gravity controlled means. Alternatively or additionally, the piston and/or a border of the aperture may be coated with a suitable coating, e.g. polytetrafluoroethylene (PTFE). Furthermore or alternatively, the gravity controlled means, in particular the ball or the cylinder, may be coated with a suitable coating, e.g. with rubber or PTFE.

Said gravity controlled means may be disposed on the side of the piston oriented to the rear part of the foot. In addition, a further gravity controlled means may be disposed on the side oriented towards the front part of the foot in order to improve the gait in a backward direction.

In order to separate both sides of the vane type piston in a fluid tight manner from each other, the hollow body or the piston may further comprise a further separating member configured to separate in cooperation with the piston the inner volume of the hollow body in two separate partial volumes. Preferably, the separating member is formed integrally with the housing and limits the partially cylindrical inner surface.

In order to improve the dynamic of the system during the swinging stage (during the foot is in the air) by compensating the pressure between the two sides of the piston during the swinging stage after releasing the load from the ankle and by moving the gravity controlled means for opening the aperture and/or to enable a further rotation of the attachment means after the aperture is closed by the gravity controlled means, the artificial ankle may be provided with a bypass channel for the hydraulic fluid which connects both partial volumes on both sides of the vane type piston. Said bypass channel may comprise a valve for opening and/or closing the bypass channel. Further, means for closing said valve upon a predetermined load to the attachment means are provided. With this configuration, the user is enabled to perform a natural gait, as the rotation of the attachment means is configured so as to rotate the shank relative to the foot as long as the user does not step on said foot, that is, as long as no load is carried out to the attachment means.

Said bypass channel and the valve may be arranged within the housing, within the separating member or within the vane type piston itself. The means for closing said valve (valve operating member) is advantageously disposed at least partially in the housing. It may be formed either as mechanically activated valve stem which can be sealed in a fluid tight manner or alternatively may be formed as magnetically or electromagnetically activating means, wherein an activating magnetic field may be generated using permanent magnets or electromagnetic devices. Such electromagnetic device may be a solenoid powered by a voltage generated by a piezoelectric device when load is applied to the inventive ankle.

Advantageously, the bypass channel and the valve are arranged within the vane type piston and the means for closing said valve is a magnetically activating means. In this case, besides the sealing between the housing means and the piston, no further sealing area exists and therefore, the probability of leakage is reduced to a minimum.

The artificial ankle additionally may be adapted so that the attachment means upon load is movable towards a valve operating member thereby pressing the valve operating member in a valve seat. If the load to the attachment means is mechanically transmitted to the valve stem, a further sealing between the attachment means and the valve stem is required.

In a preferable embodiment, a valve is used, which is operated by using magnetic coupling between the attachment means and the valve stem. Preferably, an iron ball is operated by a magnet disposed in the housing, the magnet being movable in an up- and downward direction in order to open and close the valve.

Preferably, a magnetic ball is used, which is able to roll on a cone-shaped surface. By disposing a magnet, e.g. a ring-shaped magnet, behind the cone-shaped surface, the magnetic ball is forced to a closed position.

The artificial ankle according to the invention may also include means for limiting forward and/or backward rotation of the vane type piston from a neutral position upon no load to the attachment means. The neutral position is a position, in which the sole of the foot and the shank or attachment means are bent rectangular. In order to provide the neutral position, a wedge preferably having a height of 10 mm to 12 mm may be provided on a footplate below the heel. Said limiting means may be disposed between the inner surface of the hollow body and the piston or outside of the housing.

Further, a wedge may be used in order to limit the deformation of the footplate to provide better roll-over characteristics of the prosthetic foot.

Said means are adapted so as to limit forward rotation (dorsiflexion) preferably from a neutral position in which the sole of the foot and the shank define a right angle to +30°, preferably to +20°, more preferably to +15°, and/or to limit backward rotation (plantarflexion) preferably from the neutral position to −90°, preferably to −30°, preferably to 20°, more preferably to 15°.

Said means for limiting forward and/or backward rotation may be configured as standard compression spring. Alternatively, neutralizing springs may be formed as return spring, e.g. a leg spring. The neutralizing springs may also be formed of a PU foam material inserted between the piston, preferably a projection formed on the piston, and the housing on each side of the hydraulic chamber. The returning spring may also be inserted inside the housing actuated by the relative rotation of the piston to the housing. Neutralizing springs made of PU foam material can be configured small in comparison to standard compression springs and need no further through holes in the housings. Furthermore, the PU foam used as spring further acts as seal so that no further sealing solution is necessary.

The forward and/or backward rotation can also be limited by a contact, in particular a one- or two-dimensional contact, between the housing and the piston as rigid components of the ankle or between the gravity controlled means and the housing as well as between the gravity controlled means and the piston. For example, the separating member of the housing may be formed so as to limit the rotation of the piston and act as means for limiting the forward and/or backward rotation. Alternatively, the separating member may comprise the function of the means for limiting rotation, if the separating member has projections projecting into the hollow body or if together with the cylindrical surface area it forms a hollow body having a cross section in the form of a pie slice.

The artificial ankle may include a blocking mechanism for fixing the ankle in a desired position independent from the load on the ankle. Such a blocking mechanism is suitable when the ankle is used e.g. for driving a car. The blocking mechanism is preferably adapted to assure that the ankle is kept in a predetermined position. The blocking mechanism may contain a lever turnable around an axis and at least one groove on the outer surface of the housing, the lever being adapted to engage with the groove. Dependent on the place of the groove, different fixable positions of the ankle can be achieved.

Alternatively, the attachment means may be provided with a bar containing grooves. Between the bar and the housing balls are arranged. By moving the bar, the balls are pressed into valleys in the housing. The arrest is held by a "click-clack" mechanism.

The attachment means of the artificial ankle may have the form of a fork with a joint and two arms, wherein one arm is fixed to each axial end or supporting element of the vane type piston. The use of two arms each connected towards the side wall leads to a uniform and stable motion of the vane type piston.

Besides, said fork may comprise only one arm fixed to one of the axial ends or supporting members of the vane type piston. This arrangement requires only one supporting member on one side of the rotational axis of the piston. Thus, only one sealing on one side of the housing is required. In this case an additional second arm of the fork may be rotatably supported by the opposite side wall of the housing.

In order to seal the junction between the housing and the supporting element as mentioned above a fluid tight ring seal can be used. Ring seals are known from the state of the art and are adapted not only to seal the contact between two components fixed to each other but also to seal the contact between two components moving relative to each other, such as the housing and the supporting elements, which is connected to the attachment means and the piston, for rotating the piston depending according to the position of the attachment means.

Preferably, the artificial ankle may be configured to allow a rotation of the artificial ankle threedimensionally in space, so that it is essentially on an ankle-joint compensation plane (Henke's axis).

As an alternative or addition, this may be e.g. achieved by using two plastically coupled pistons, having different blocking angles. The different blocking angles effect the supporting elements on both sides of the housing to rotate to different positions so as to rotate the ankle relative to the leg. Such a configuration results in reduction of the rotational load on the leg stump of the user.

The present invention further relates to an artificial foot comprising a foot plate and an ankle joint. Said ankle joint comprises a housing with a hollow body for retaining or comprising a hydraulic fluid, the hollow body having a partially cylindrical surface area, a vane type piston having an aperture to allow the hydraulic fluid to move between both sides of the piston, the piston being arranged in the hollow body and being pivotable about the rotational axis of said cylindrical surface area in a sealing manner with at least said cylindrical surface, thereby separating in a fluid tight manner both sides of the vane type piston. Further, the ankle includes gravity controlled means for opening and closing said aperture of the vane type piston, at least one supporting element connected to axial ends of the piston to form together with the housing the hollow body and attachment means for attaching a shank to the artificial ankle said attachment means being fixed outside of the hollow body to the piston. The vane type piston and the gravity controlled means of the artificial ankle are configured to close the aperture when the attachment means is in a position so as to fix a shank in a substantially vertical position.

In the artificial foot according to the invention, the foot plate is attached to the housing of the ankle which is configured so as described above.

Said artificial foot may comprise means to adjust the relative position of the housing of the ankle and the footplate. Such means may be configured as adjustment screw seated in the ankle or the footplate and acting on the footplate or ankle respectively. By turning said adjustment screw, preferably disposed at the front-side of the housing, the stiffness of the fore-foot and the neutral angle of the prosthetic foot can be adjusted.

The foot plate comprises preferably a fore-foot plate and a back-foot plate, said foot plate being advantageously made of fibre-reinforced composites, e.g. carbon fibre, vectran. Additionally, the footplates may be made of fibre-reinforced composites with a core made of different materials, e.g. with directionally oriented structure, to enhance 3D-roll-over characteristics of the foot parts.

The shape of the carbon fibre fore-foot plate and the carbon fibre back-foot plate may be configured to bend into a circular shape providing better energy storing and returning effects but has a maximum stop of the deformation by the housing. The fore-foot plate and the back-foot plate can be connected to each other. Said connection can be achieved by at least one screw, a metallic hook and loop fastener or any suitable adhesive. The fore-foot plate and/or the back-foot plate can thereby be adapted so as to displace the fore-foot plate relative to the back-foot plate in order to adjust the stiffness characteristics of the heel. In case of a connection by screws, the fore-foot plate and/or the back-foot plate can thus be provided with a slot hole. In case of a metallic hook and loop fastener, the connection may be easily loosened and reconnected as desired.

The present invention further relates to an artificial leg comprising an artificial foot which contains an ankle and a footplate configured such as explained above, and a shank. The shank is attached to the attachment means in substantially straight alignment with the attachment means.

Figure 4A:
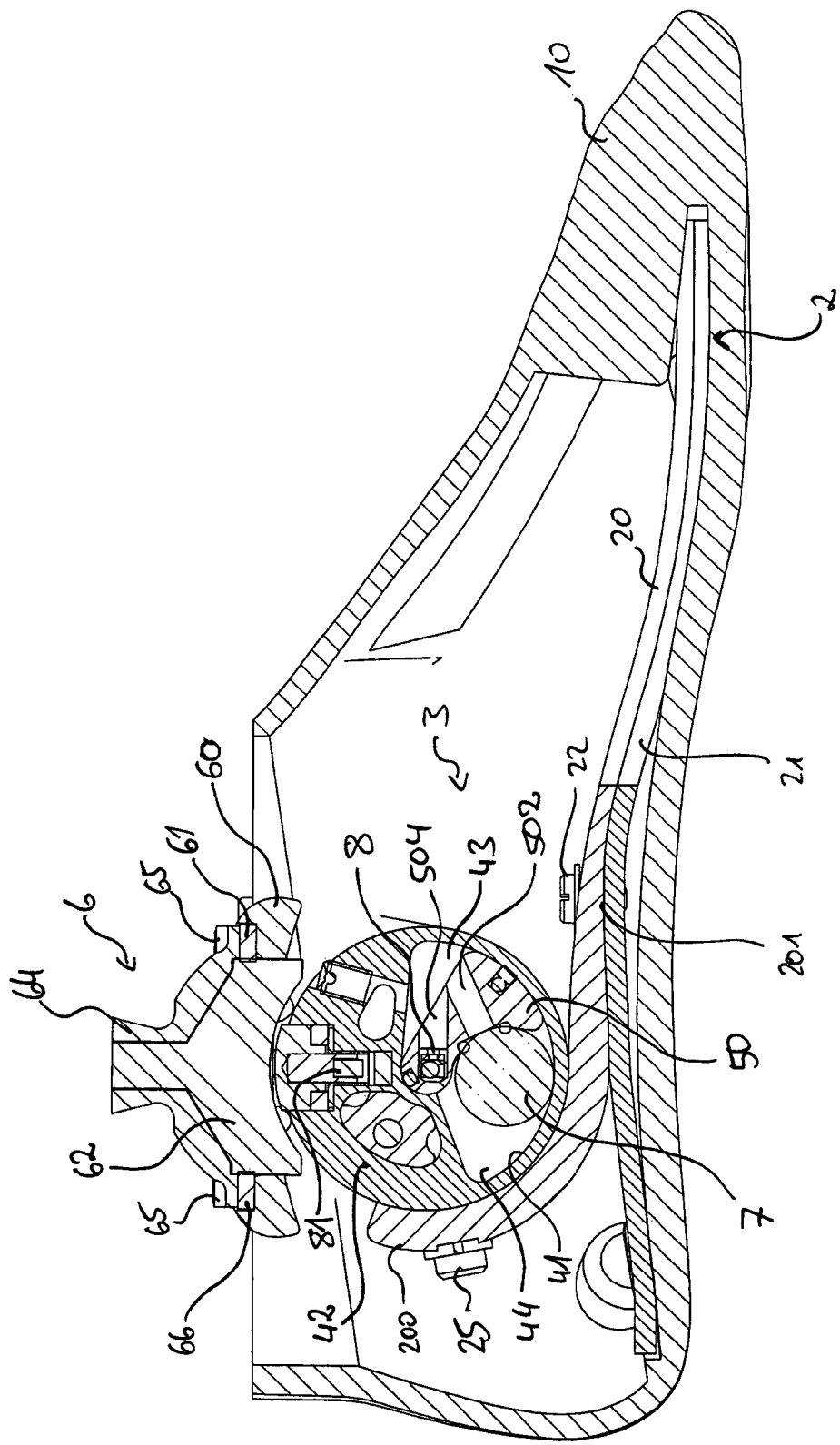
Figure 4B:
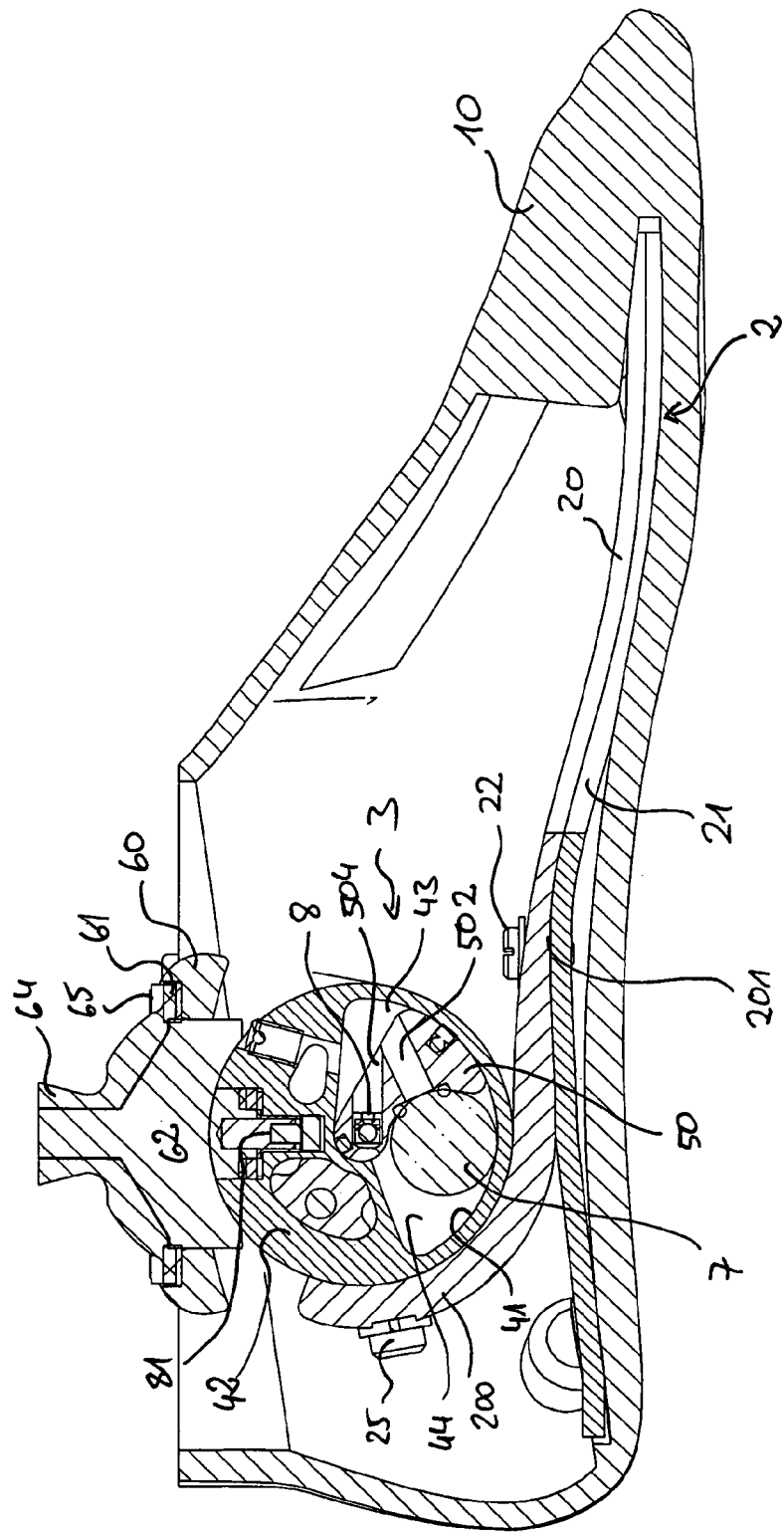
Figure 5:
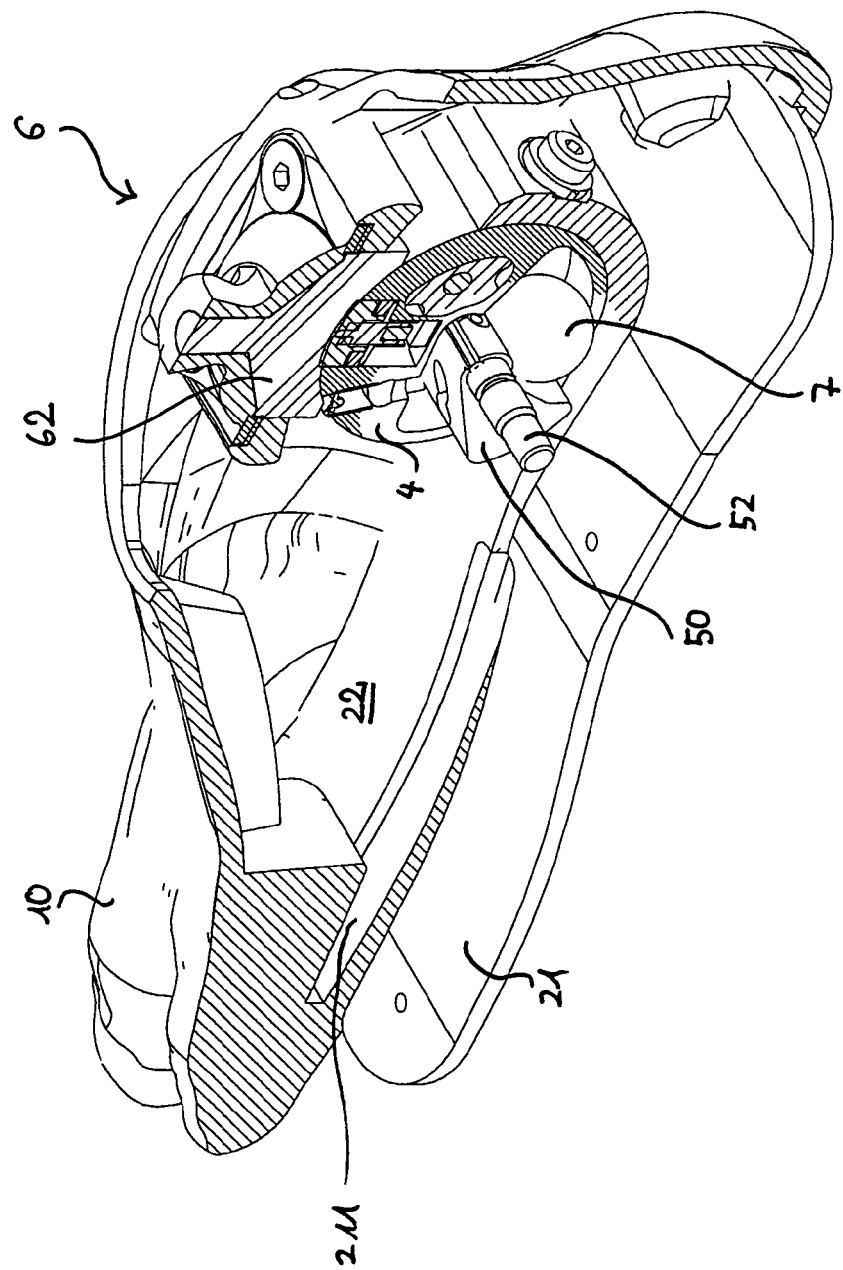
Figure 6A:
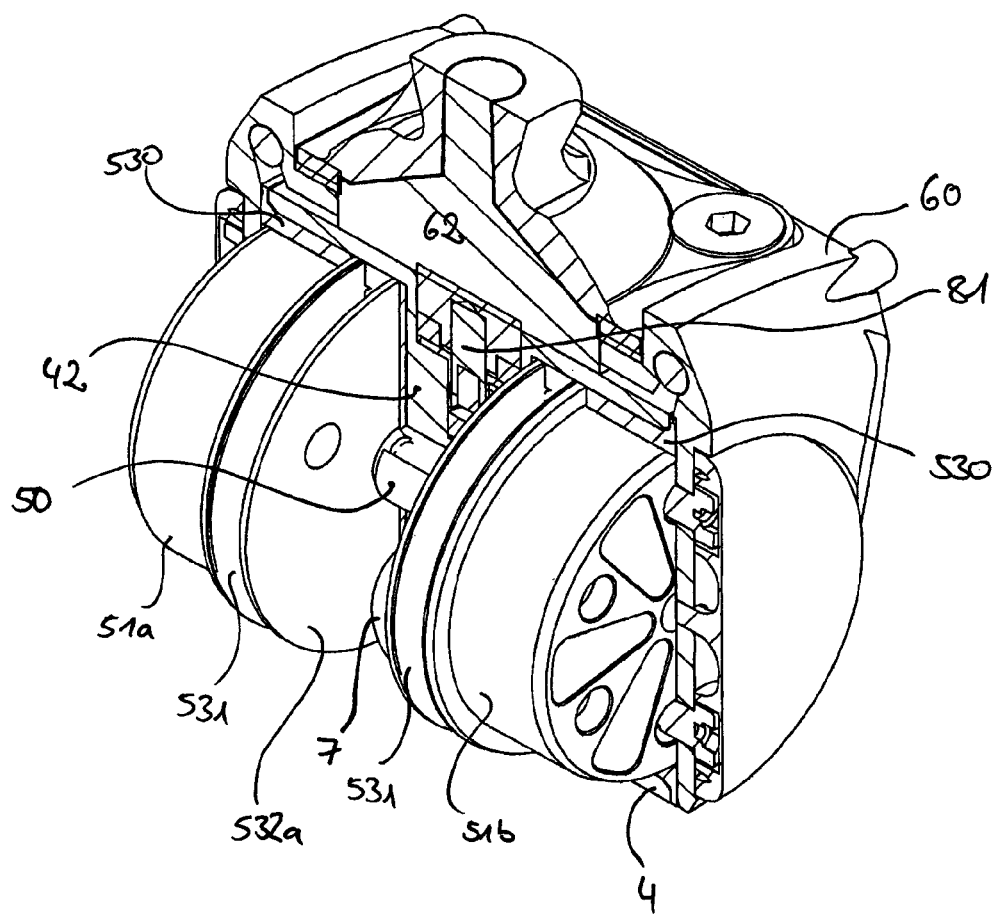
Figure 7:
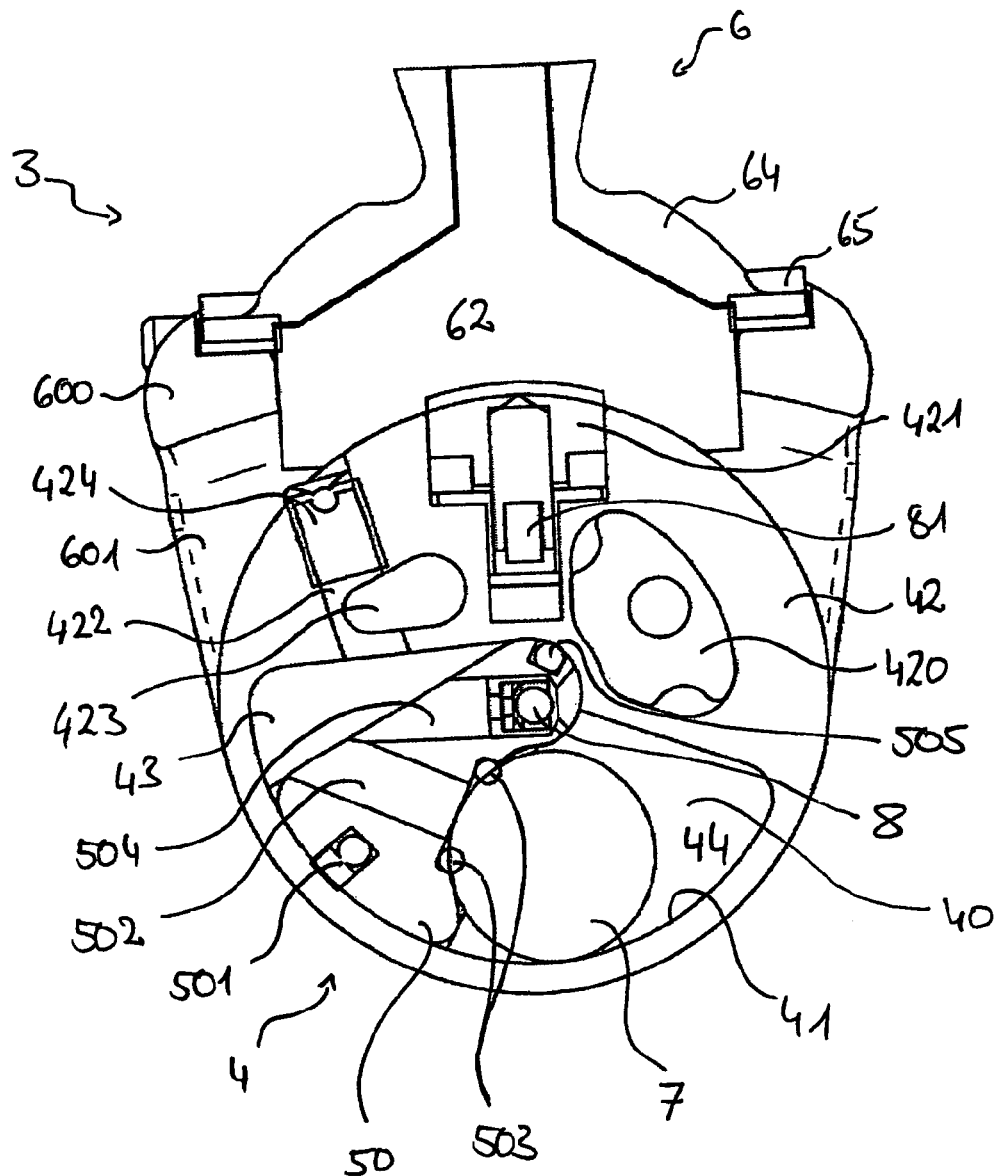
Figure 8A:
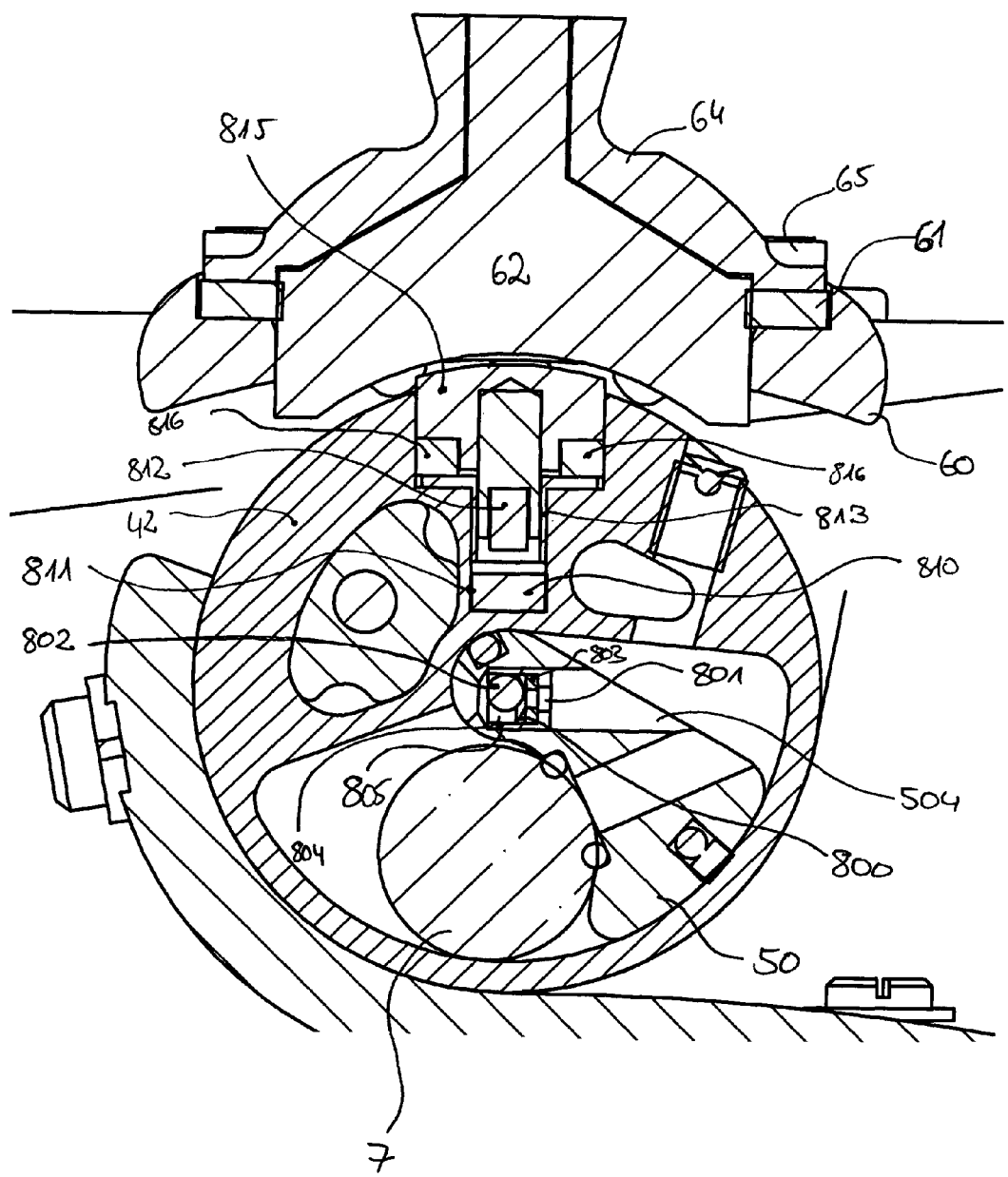
Figure 9A:
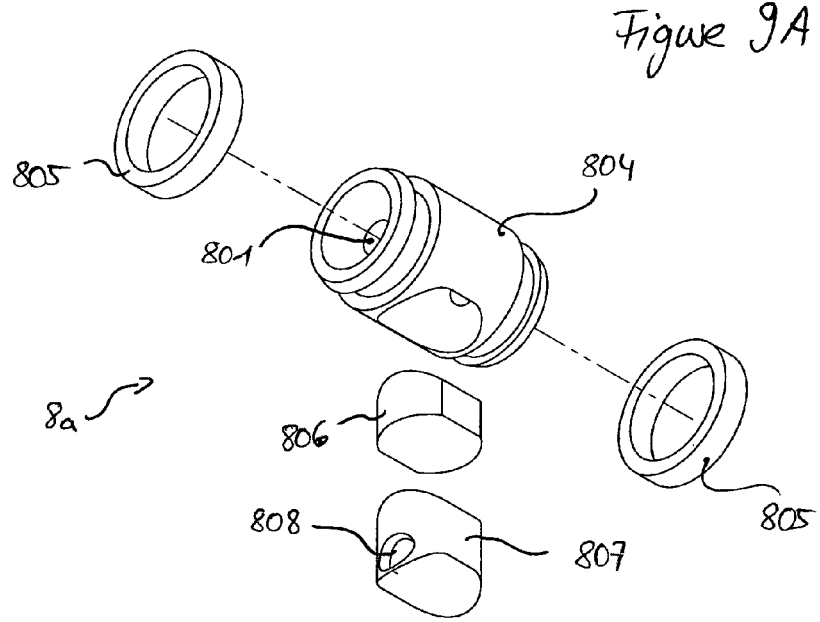
Figure 9B:
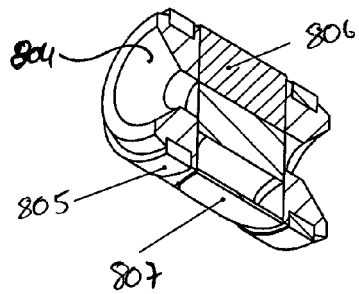
Figure 9C:
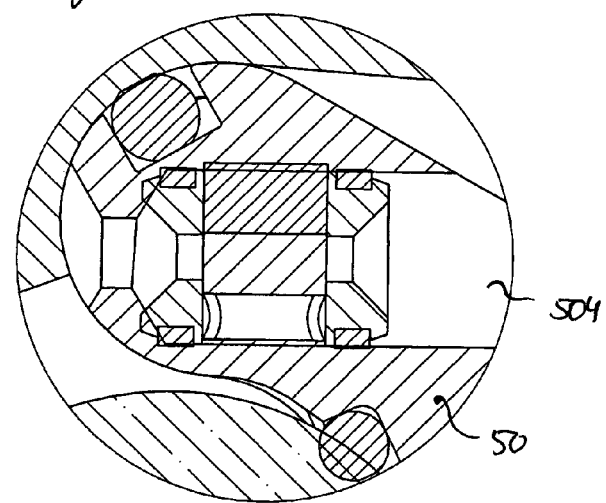
Figure 10A:
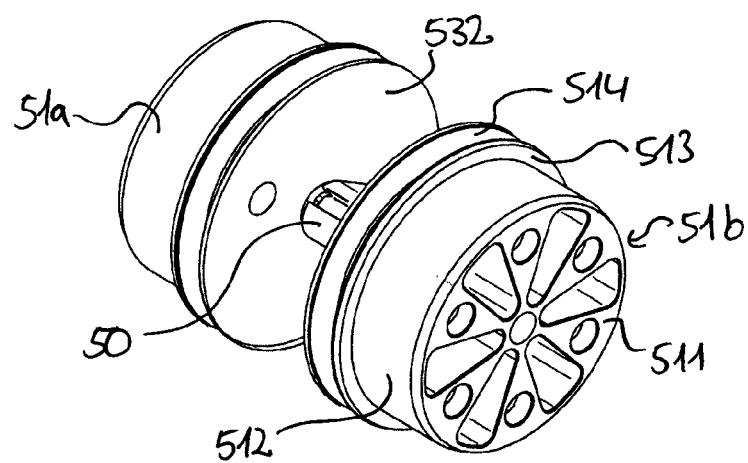
Figure 10B:
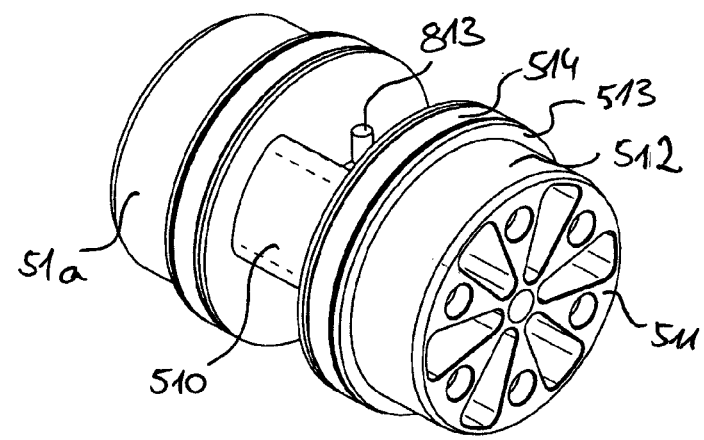
Figure 10C:
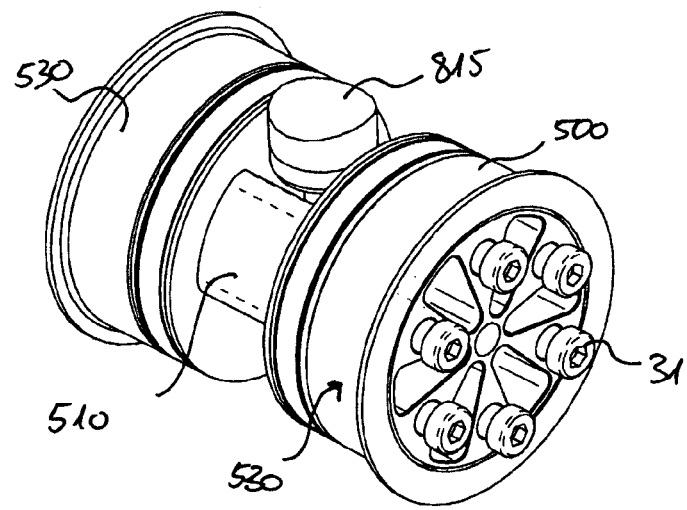
Figure 11A:
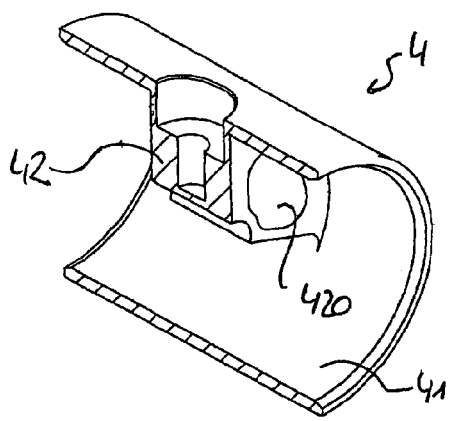
Figure 11B:
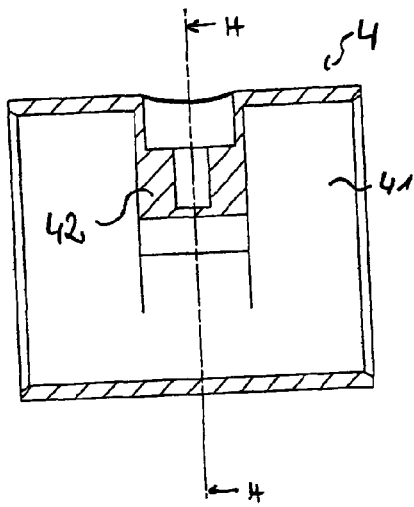
Figure 11C:
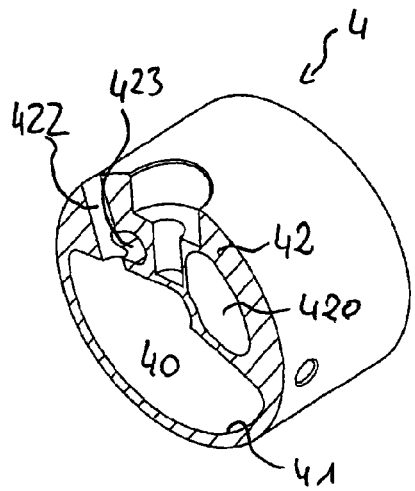
Figure 12A:
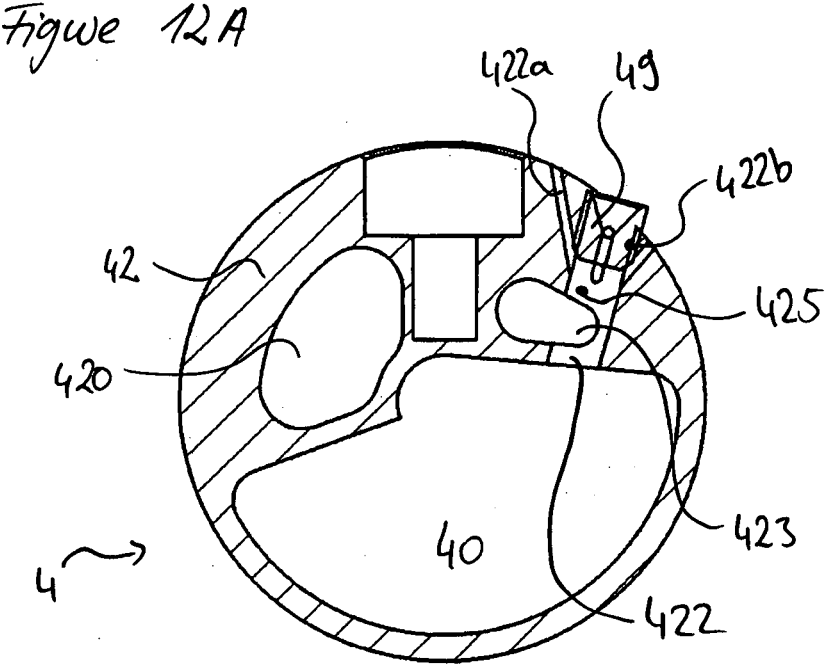
Figure 12B:
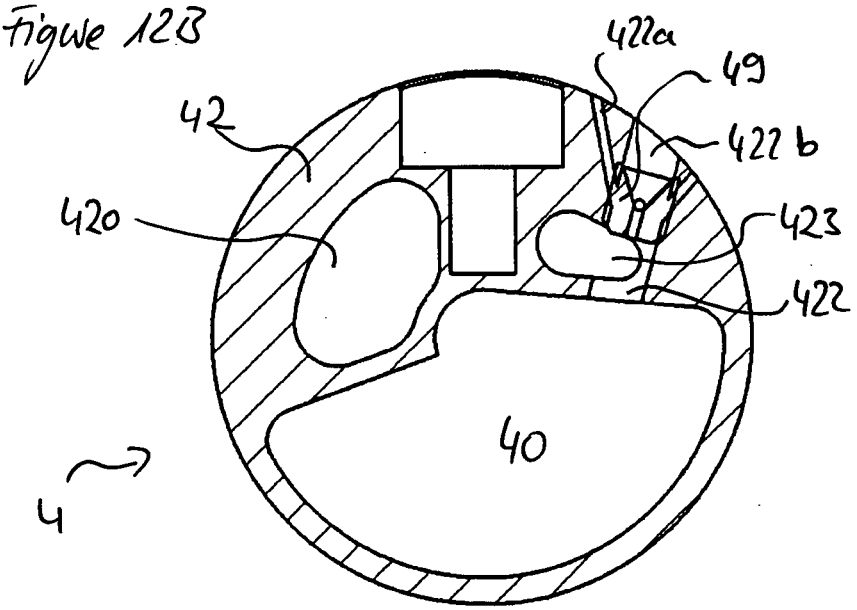
Figure 14A:
Figure 14B:
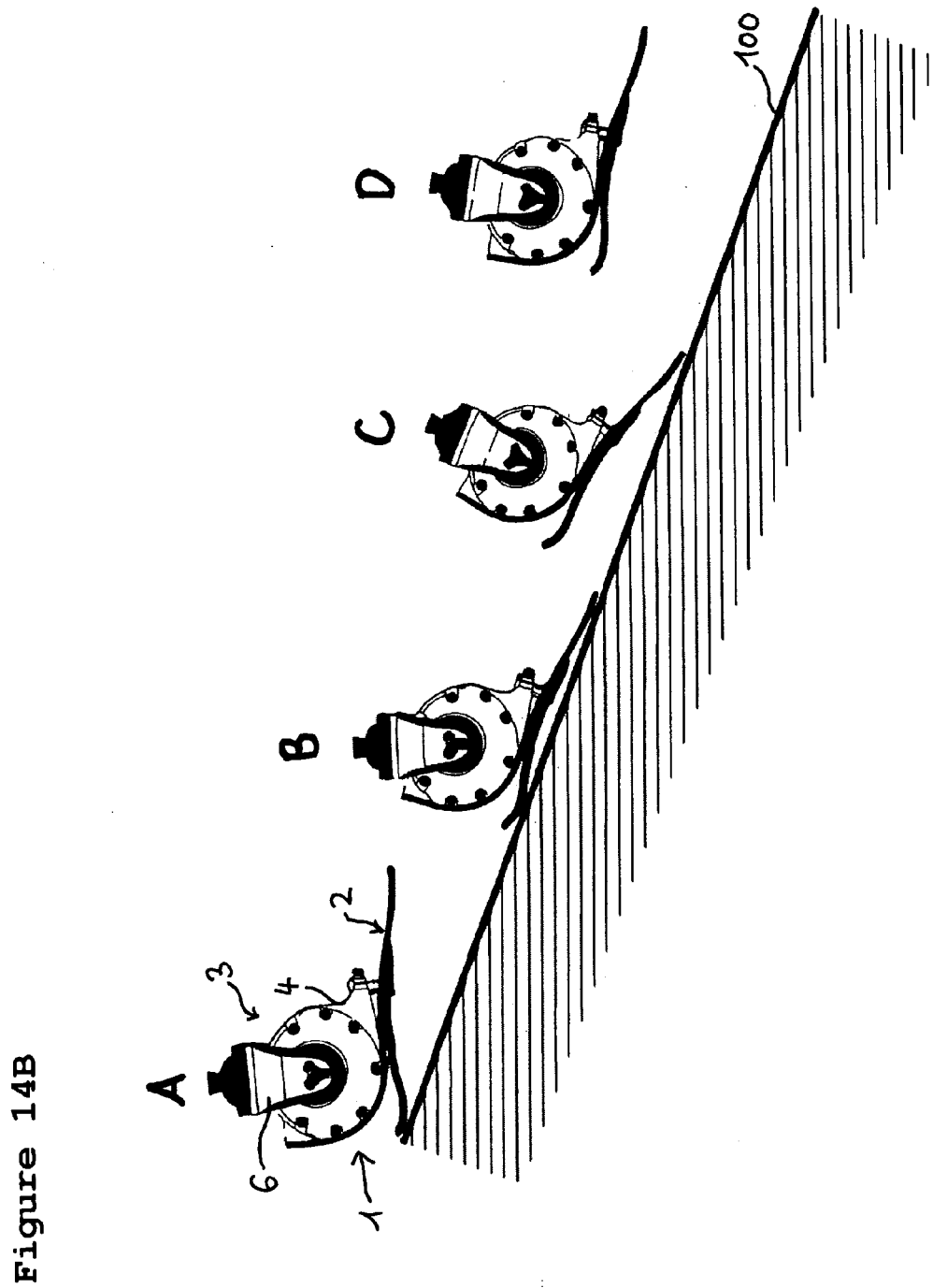
Figure 15:
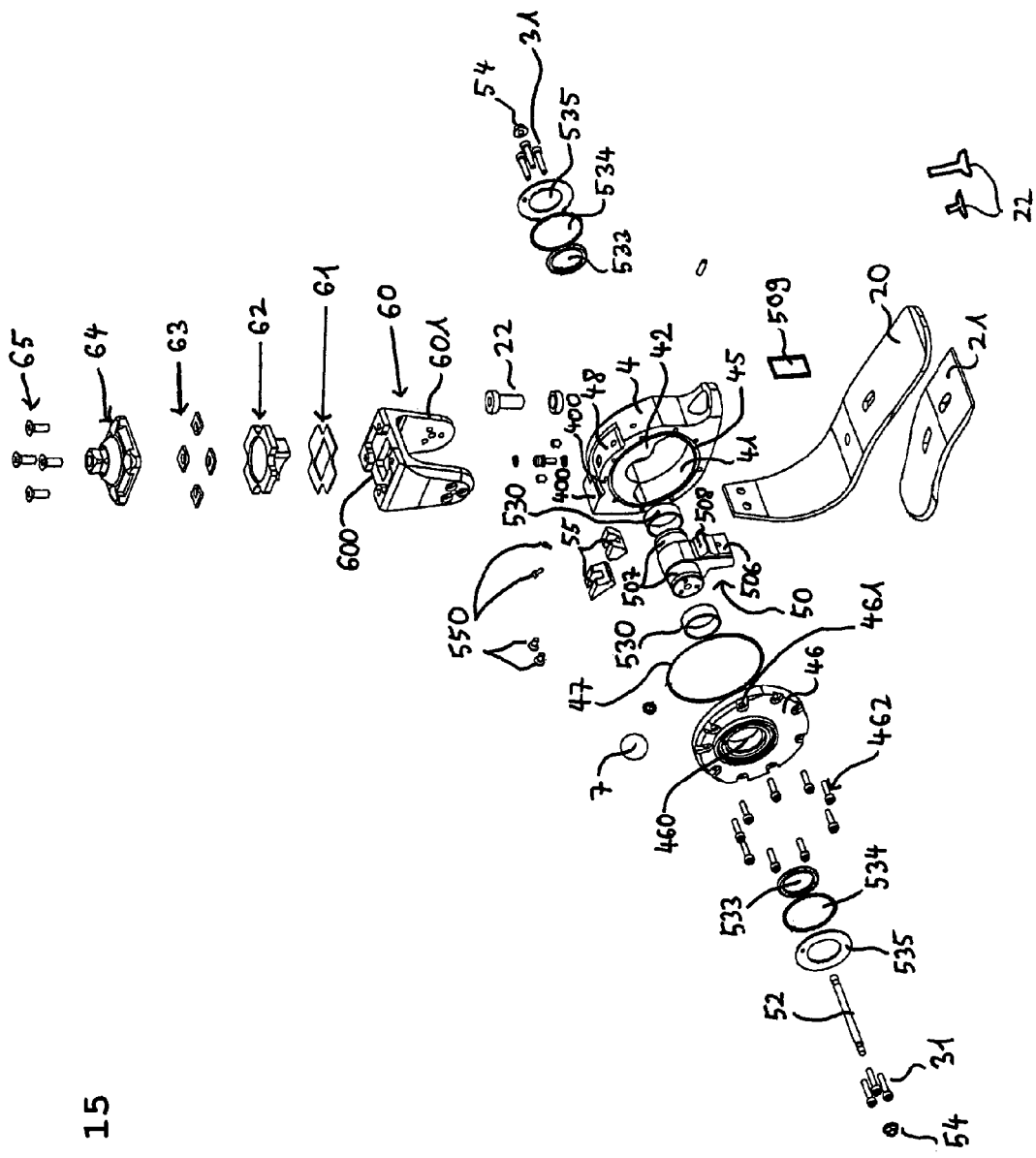
Figure 16:
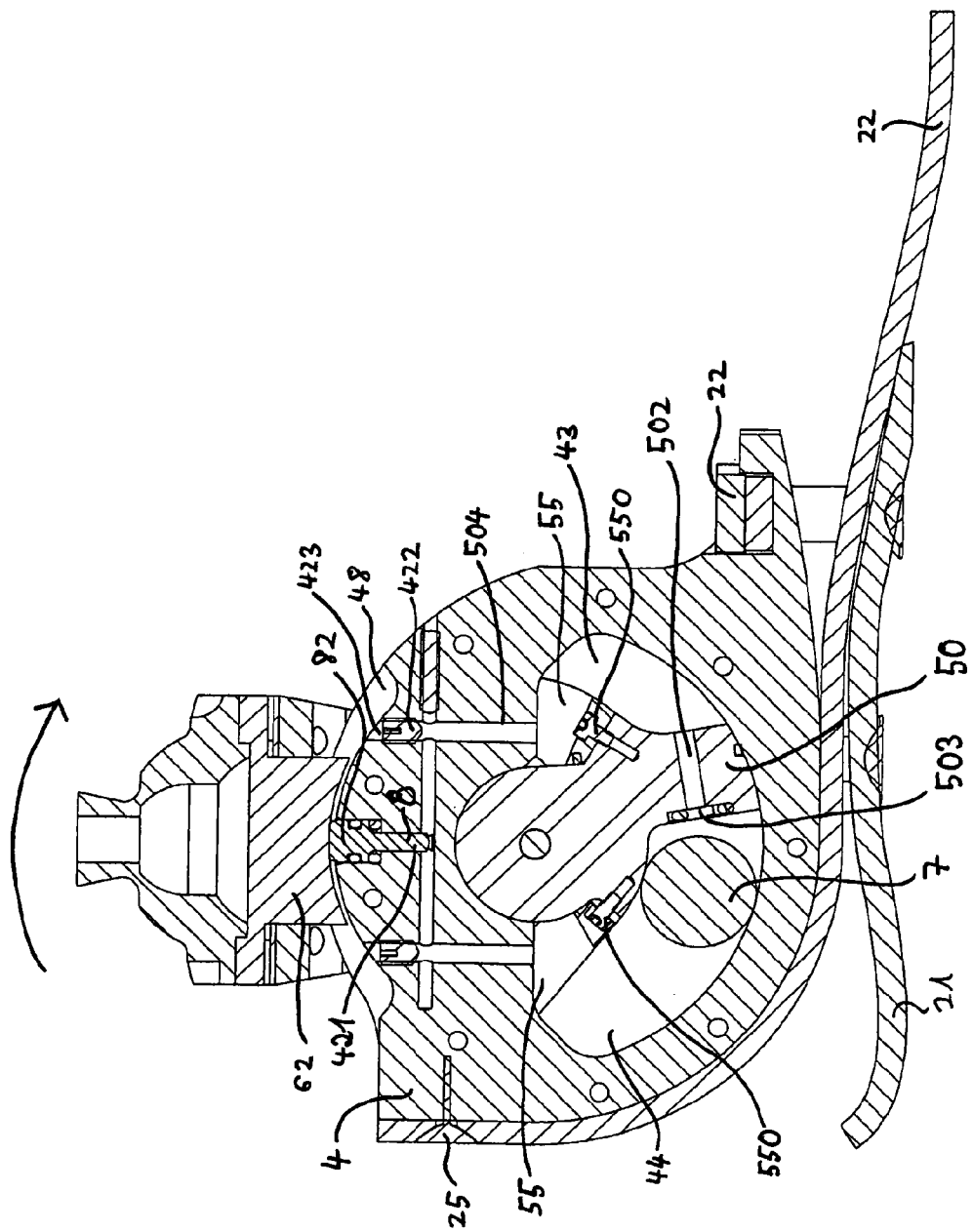
Figure 17A:
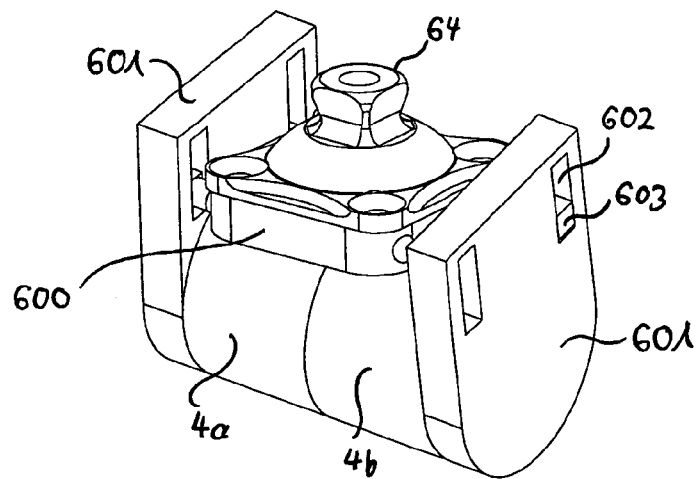
Figure 17B:
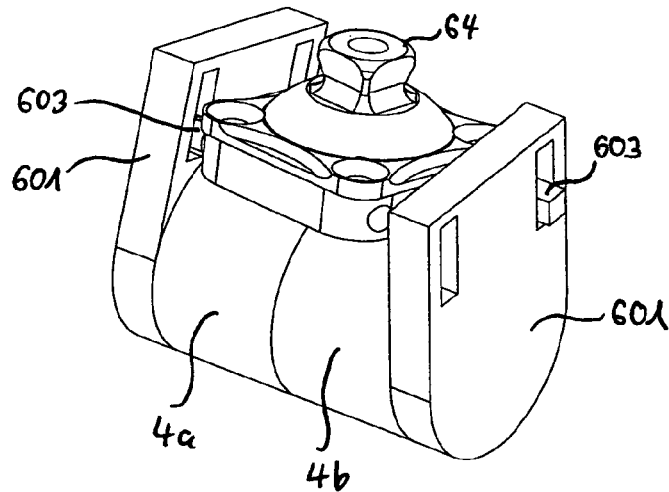
Figure 17C:
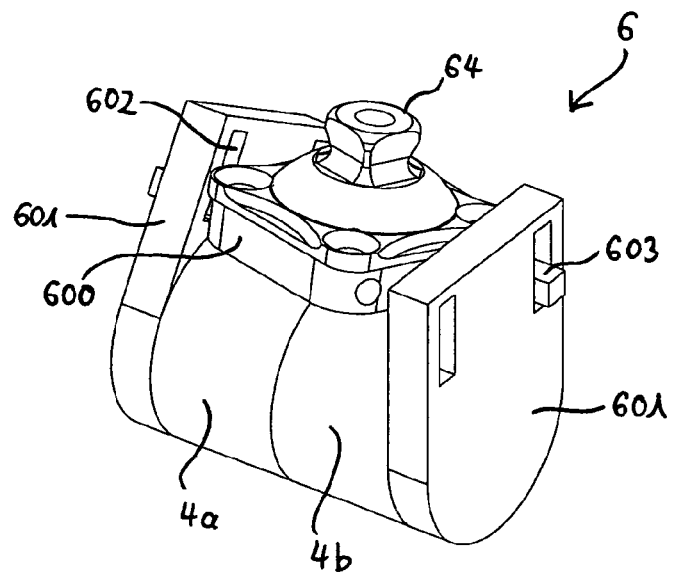
Figure 18:
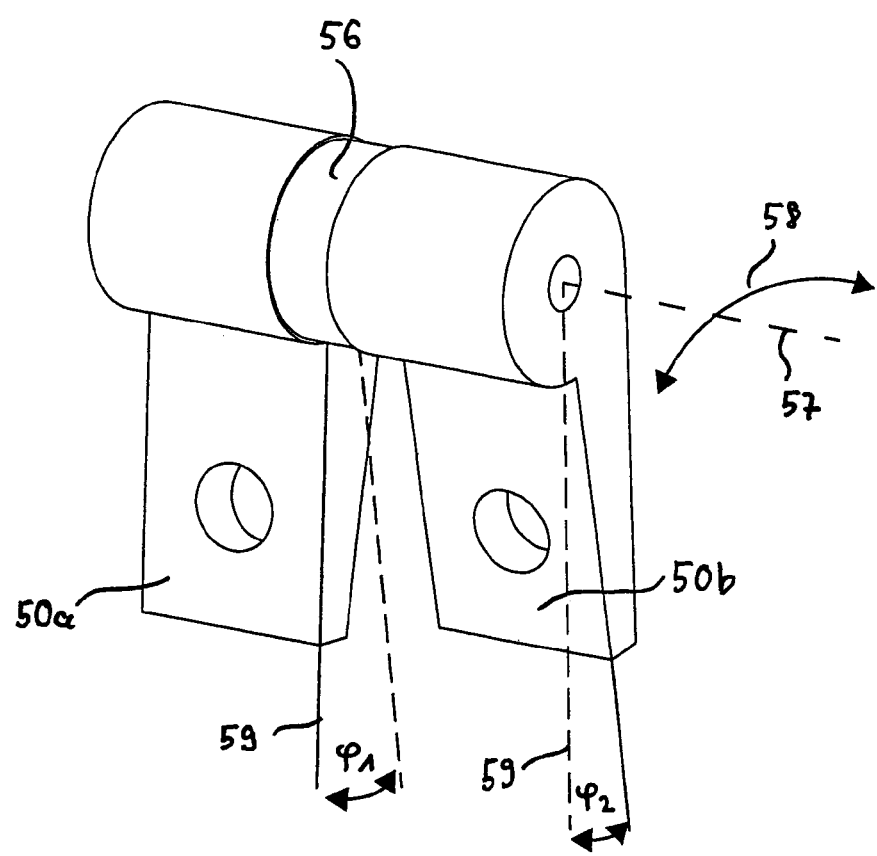
Figure 19:
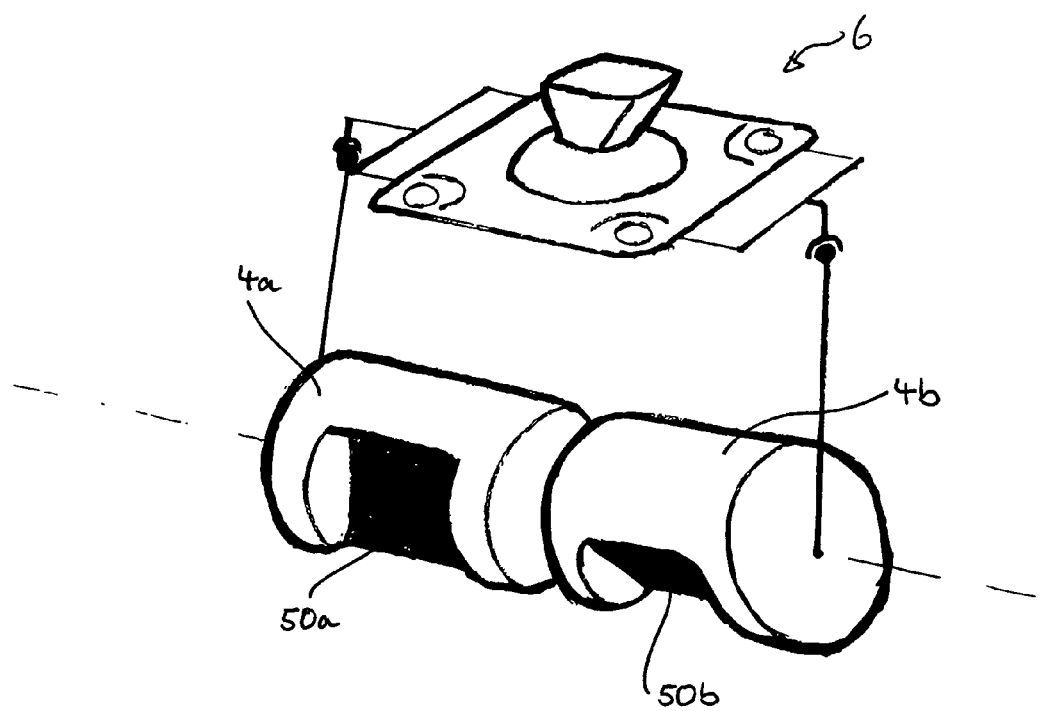
Figure 20:
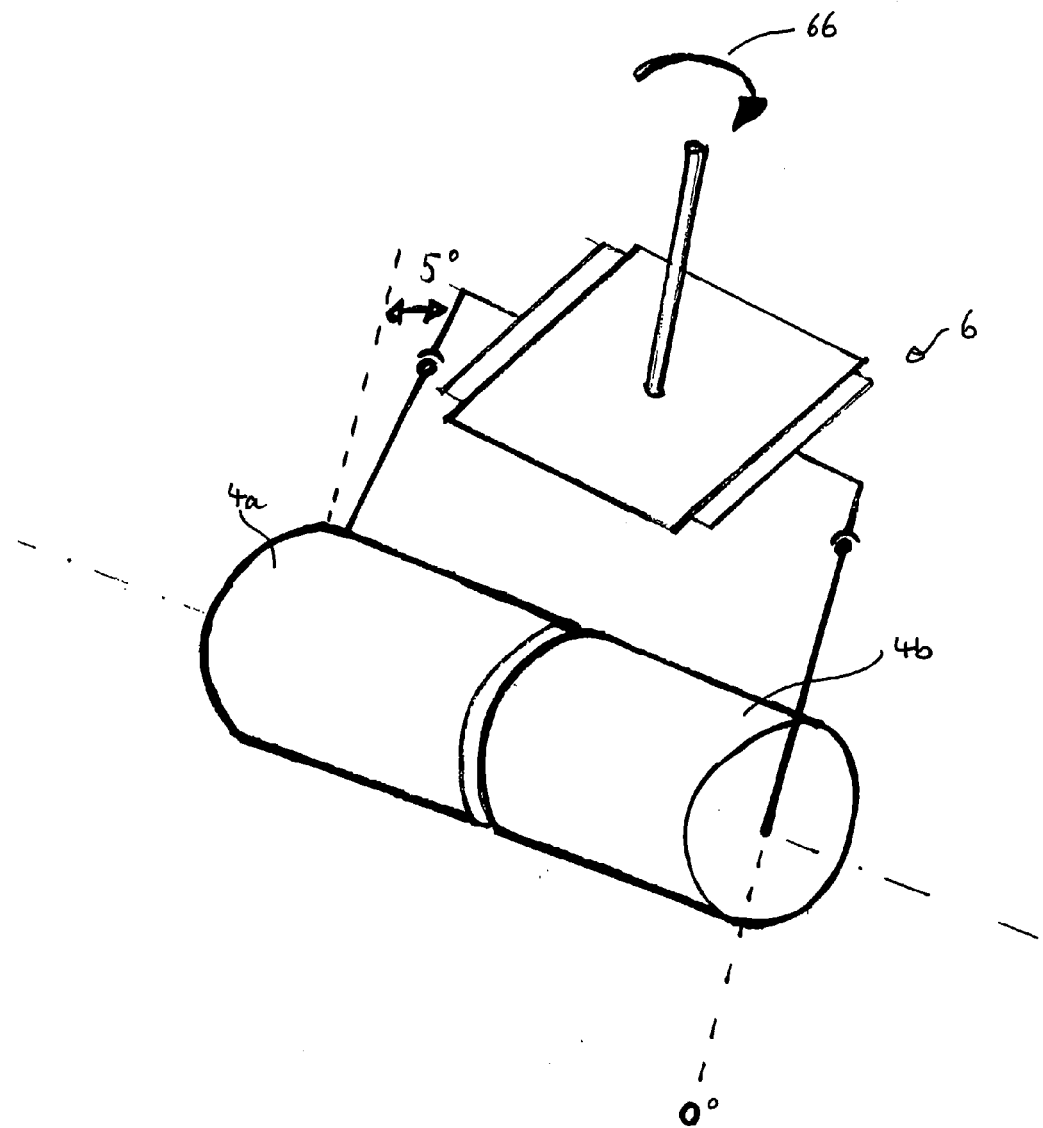
Figure 21:
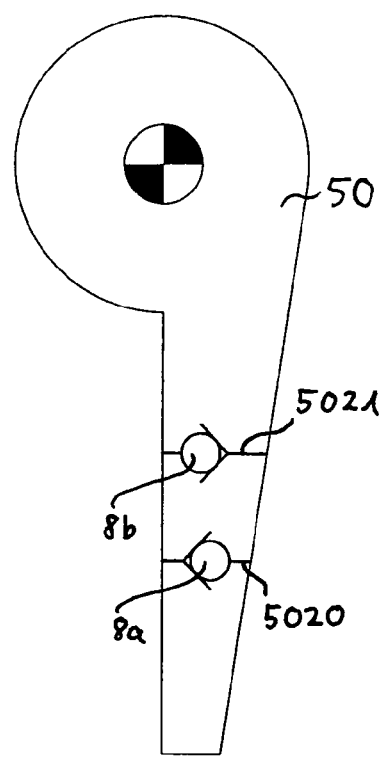

In the following, the present invention is described with reference to embodiments of the invention based on the following drawings. Therein, several and different aspects of the invention are described in combination with each other although they may be employed separately from each other. In the figures same or similar elements are designated by same or similar reference signs. In the following show:

FIGS. 1A-1B a perspective view of an artificial foot and an artificial heel;

FIG. 2 an artificial foot according to the invention within a transparent cover;

FIG. 3 an exploded view of an artificial foot according to the invention;

FIGS. 4A-4B the side view of a longitudinal cut through the artificial foot of FIG. 1B with an open and a closed bypass;

FIG. 5 a partially perspective view of the artificial foot of FIG. 4A;

FIGS. 6A-6B an artificial ankle according to the invention in perspective view and in front view;

FIG. 7 a side view of the artificial ankle along the cut A-A in FIG. 6B;

FIGS. 8A-8B an enlarged view of an open and a closed magnetic valve;

FIGS. 9A-9C views of a further magnetic valve of an artificial ankle;

FIGS. 10A-10C perspective views of the piston of the artificial ankle of FIG. 7;

FIGS. 11A-11C cross sectional views of the housing of the artificial ankle of FIG. 7;

FIGS. 12A-12B filling mechanism for an ankle of the invention;

FIGS. 13A-13E the view of an artificial foot according to the invention with different positions of the attachment means;

FIGS. 14A-14B the adaption of an artificial foot to uneven terrain;

FIG. 15 an exploded view of an artificial foot according to the invention;

FIG. 16 a perspective view of the artificial foot shown in FIG. 15;

FIGS. 17A-17C exterior view on a further artificial ankle of the invention having two pistons;

FIG. 18 relative turning of the two pistons of the artificial ankle according to FIGS. 17A-17C;

FIG. 19 further view on an artificial ankle having two pistons;

FIG. 20 rotation of the attachment means depending on the relative rotation of the pistons;

FIG. 21 piston having a two-way flow control; and

Figure 22:
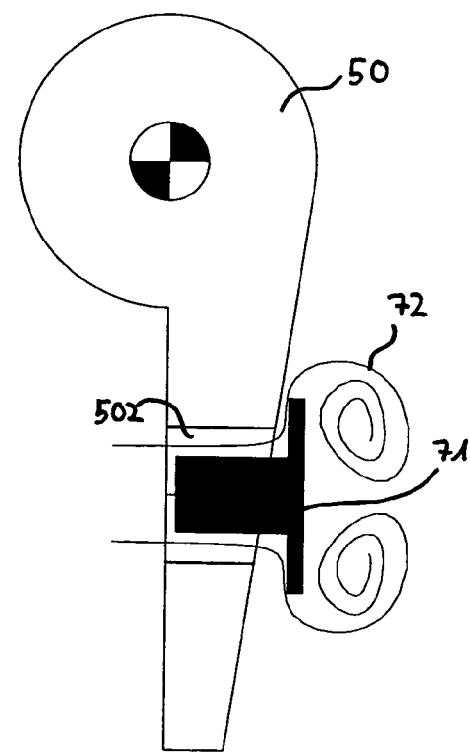

FIG. 22 mechanism for controlling the flow velocity.

FIG. 1a shows a perspective view of an artificial foot 1 according to the invention. Said artificial foot 1 contains a cover 10 in the form of a human foot. In the area of the human ankle, said cover 10 is open and it appears that said cover 10 covers an artificial ankle 3 with its attachment means.

In FIG. 1b, the artificial foot 1 is presented from the heel part of foot 1. Said artificial foot 1 includes—as already shown in FIG. 1a—cover 10 and attachment means 6 of the ankle 3 projecting from the cover 10. FIG. 1b further indicates a cutting axis A-A in a vertical direction.

In FIG. 2, cover 10 is shown in an almost transparent manner. Said cover 10 covers footplate 2 which is attached to the artificial ankle 3. Said footplate 2 contains an upper fore-footplate 20 having an upwardly bend heel part 200 attached to a housing 4 of the artificial ankle 3. Said footplate 2 further includes a lower back-footplate 21 forming the sole of the foot including a heel part 210 disposed under the artificial ankle 3 which acts as heel spore. The fore-foot plate 20 and the back-foot plate 21 are connected to each other in a position, where the metatarsus 201 and the foot-toes 202 are positioned in a human foot, by using screws 22. Alternatively, the fore-foot plate 20 and the back-foot plate 21 may be connected to each other by using a suitable adhesive or a metallic hook and loop fastener.

Said fore-foot plate 20 and said back-foot plate 21 are made to have elastic properties, which can be adjusted by adjusting the length of the heel part 210 of the back-foot plate 21, the width of the material or by using different material levers.

Only the outer parts of the artificial ankle 3 are shown in FIG. 2, namely a housing 4 formed as cylinder and the attachment means 6, containing side portions 601. Said side portions are formed as one piece with a frame 60 of said attachment means 6 and are covered by a face plate 30. The inner configuration of the artificial ankle 3 is described with respect to the following figures.

FIG. 3 shows the explosion view of the artificial foot of FIG. 2. In the lowest part of the figure, the cover 10 formed with a surface according to that of a human foot is shown. Above said cover 10, the back-foot plate 21 and the fore-foot plate 20 with its bend heel part 200 are presented. Above the foot plate the screws 22 and discs 220 for connecting the fore-foot plate 20 and the back-foot plate 21 to each other are shown. Atop the fore-footplate 20, a cylindrical housing 4 oriented with its rotational axis in a horizontal plane is shown, which has a cylindrical inner surface 41 and a separating member 42 for forming a hollow body. The housing is further provided with a bore hole 49 on top of the cylindrical housing 4 and a throughhole 422 for filling the hollow body with hydraulic fluid covered with a plug 424. Said housing 4 is to be mounted to the heel part 200 of the fore-foot plate 20 using the screws 25 and the discs 26.

On the left side of the housing 4, a return spring 510 and a bolt 5100 for said return spring 510 are shown, which can be positioned into an opening 420 in the separating member 42. On both sides of the housing 4 a seal plate 532a, 532b, a ring seal 531, a supporting element in the form of a side plate 51a, 51b provided with bars and grooves along the periphery of their lateral area as will be described with respect to FIGS. 10a to 10c in more detail and acting as supporting element, a slide bearing 530, screws 31 and a plastic face plate 30 are presented. The left side plate 51a is provided at its face side oriented towards the housing 4 with a vane-type piston 50 and a pin 52. The piston 50 has a similar form as a pie slice, wherein the rounded edge portion is adapted to the form of the cylindrical surface area 41 and provided with a groove for a seal strip 501 and the edge next to the pin 52 is rounded off so as to fit in a recess of the separating member 42 and also provided with a groove for a seal strip 505. The piston is provided with an aperture (not shown) and a bypass 504, wherein the bypass 504 can be provided with a valve 8.

The seal plate 532a to be placed adjacent to the side plate 51a has a hole for the bolt 5100 and a recess in the form of the cross section of the vane-type piston 50. The seal plate 532b neighboured to the side plate 51b is provided with a hole for the bolt 5100 and a central hole for the pin 52. Between the seal plate 532b and the side plate 51b a ring seal 536 for the pin 52 and a nut 54 to be fixed with the pin 52 is shown. All components presented between the two slide bearing 530 including a gravity controlled means comprising a ball 7 are to be assembled within the housing 4 and the side plates 51a, 51b, the seal plates 532a, 532b and the ring seal 536 are fixed by the pin 52 and the nut 54.

The screws 31 are used for mounting the frame 60 of the attaching means 6 to the side plates 51a, 51b and can be covered by the face plate 30.

FIG. 3 further shows the components of the valve operating member 81 containing an induction disc 810, a induction disc duct 811, a bar magnet 812, a bar magnet duct 813, a channel 814 and an operating cap 815. When load is transmitted to the operating cap 815, the bar magnet 813 is moved downwards and therewith enabled to lift the induction disc 811, which moves a magnetic component in the valve 8 so as to close the valve 8. This configuration of the valve and alternative configurations will be presented in more detail with respect to FIGS. 8A to 8B and 9A to 9C.

At least FIG. 3 shows the attachment means 6, which contains a frame 60 having a basic portion 600 and the side portions 601 having six holes for the screws 31 to fix the side plates 51a, 51b of the rotational piston to said frame 60. The attachment means 6 further contains a bumper 61, an underbody 62 and a pyramid adapter 64 which is fixed to the frame 60 using four screws 65.

As will be shown later in more detail, the ball 7 and all components of the rotational piston are disposed within the hollow body 40 of the cylindrical housing 4 when the ankle 3 is in its end configuration. The side portions 601 of the frame 60 are then put over the vertical end faces of the housing 4.

FIGS. 4A and 4B show a cross-sectional view of the artificial foot 1 shown in FIG. 3, where FIG. 4A presents the valve 8 in the bypass 504 in an open (a ball is above the valve seat and the flow channel is open) state and FIG. 4B presents the valve 8 in a closed state (the ball sits in the valve seat and stops the flow). Again, the foot plate 2 connected to the artificial ankle 3 disposed within the cover 10 is presented. The artificial ankle 3 is shown in an assembled configuration.

The fore-footplate 20 is mounted on the back-foot plate 21 in the metatarsus area 201 by the screws 22. The back-foot plate 21 and/or the front-foot plate 20 can have longitudinally sustained bores, so that the fore-foot plate 20 and the back-foot plate 21 can be displaced relative to each other in order to adjust the stiffness of the foot 1.

The fore-footplate 20, which is bent upwards at its heel part 200, is connected at said heel part 200 to a part of the cylindrical housing 4 directed away from the metatarsus part 201 of the fore-foot 20 by the screw 25. Furthermore, the screws 22 in the front-foot portion strain the fore-foot with the housing, so that the portion of the fore-foot oriented towards the ground is bent to the housing and a neutral angle is moved in a forward direction (dorsiflexion). Furthermore, the fore-foot is strained stronger.

The housing 4 forms the hollow body 40 having a cylindrical inner surface 41 and a separating member 42 which both border the hollow body 40. Within said hollow body 40 the vane-type piston 50 is disposed, which is provided with the aperture 502 and the bypass 504 to be closed and opened by the valve 8 operated by the operating member 81 disposed within the separating member 42. The piston 50 separates the hollow body 40 in a fore chamber 43 and a back chamber 44, the back chamber 44 accommodating the ball 7. Further details of the piston 50, the separating member 42 and the valve 8 will be described below.

FIGS. 4A and 4B further show the attachment means 6 mounted with the frame 60 to the side plate of the housing 4. Within the frame 60 and the pyramid adapter 64 connected to each other by the screws 65, an elastomeric pad 1 for providing a labored restoring force is disposed. Within the frame 60 and the adaptor 64, an underbody 62 is arranged which is configured to transmit the load from the attachment means 6 to the operating member 81 of the valve 8.

FIG. 5 shows a partially three-dimensional cross-sectional view of the artificial foot 1 shown in FIGS. 4A and 4B. The back-footplate 21 which has an elongate open area 211 in the region of the tooth is shown in its entirety. On said back-footplate 21 is disposed the fore-footplate 20 only a half of which is shown. Said fore-footplate 20 is connected to the cylindrical housing 4 showing the same components as in FIGS. 4A and 4B in a perspective view, wherein only the vane type piston 50 and the pin 52 which is disposed along the rotational axis of the housing 4 are presented in its entirety. Furthermore, the attachment means 6 as already described in connection with FIGS. 4A and 4B is shown.

FIG. 6A displays the artificial ankle 3 according to the present invention in a perspective view, wherein the housing is partially cut. The identical artificial ankle is presented in a front view by FIG. 6B, wherein the cylindrical housing 4 in this example is transparent.

Within said housing 4, the rotational piston is disposed. Said rotational piston contains the side plates 51a and 51b, of which only bars disposed on their lateral area are shown. Said side plates 51a, 51b are covered by the slide bearings 530, adjacent to which—separated only by one of the bars of the side plates 51a, 51b—the sealing ring 531 is disposed within a groove of the side plates 51a, 51b. Furthermore, the seal plates 532a, 532b are shown on the side of the ring sealing 531 which are disposed opposite to each other. Between said seal plates 532a, 532b, the ball 7 and the vane-like piston 50 are disposed within the hollow body, which is limited by the cylindrical surface of the housing 4 and the separating member 42 (not shown in this figure, as the housing in FIG. 6B is transparent). FIG. 6B further shows the elastomeric return spring 510 for moving the vane-type piston 50 into a neutral position after release of load so that the artificial foot 1 is substantially rectangular bent when the load is taken off the ankle 3. The return spring 510 is an elastomeric material which is attached to the bolt 5100. When the rotational piston is rotated relative to the housing 4, the elastomeric material is pressed between the wall of the opening 420 (not shown in FIG. 6B) and the bolt. After a release of load, the elastomeric material extends, thereby removing the foot into the neutral position.

FIGS. 6A and 6B further show the operating member 81 for the valve 8 which is in contact with the underbody 62 of the attachment means 6. The housing 4 is partially covered by the attachment means 6, the frame 60 of which is put over at least the faces of the cylindrical housing 4.

FIG. 6B further shows a cutting line A-A along a vertical direction. FIG. 7 shows the cross-sectional view of the artificial ankle 3 along the cutting line A-A shown in FIG. 6B. As already described with respect to FIGS. 4A and 4B, the hollow body 40 within the cylindrical housing 4 is built by the cylindrical surface 41 and the separating member 42, the separating member 42 defining together with the cylindrical surface 41 the hollow body 40 which has a cross-section substantially in the form of less than a half-circle, having a cyclic recess for a rounded part of the vane-type piston 50 at the separating member 42.

The separating member 42 includes the opening 420 for the return spring 510 for resetting the vane-type piston 50 in a phase of no load to the neutral position, a recess 421 for the operating member 81 and the through hole 422 including a further opening 423. The recess 421 is arranged adjacent to the rotational axis of the housing 4 but is separated by a wall from the hollow body 40 next to which the operating member 81 is arranged. Further, the recess 421 builds the hole 49 on the lateral area of the housing 4. Via said hole 49 load can be transmitted by the underbody 62 to the operating member 81 and to the valve 8. The through hole 422 is configure to charge the hollow body 40 with hydraulic fluid and is closable with a plug or screw 424. The further opening 423 is provided to buffer a reserve of hydraulic fluid and to gather air bubbles leaving the hollow body 40.

Within the hollow body 40, the vane type piston 50 is disposed. Said vane type piston 50 divides the hollow body 40 into the fore-chamber 43 and the back-chamber 44. In order to assure, that the fore-chamber 43 and the back-chamber 44 are fluid tight sealed from each other, the piston 50 is provided the seals 502, 505 arranged within grooves at the part in contact with the cylindrical surface area 41 and at a rounded part in contact with the separating member 42.

Optionally, the fluid can also be pumped into the hollow body using a grease gun and a grease nipple which will be screwed into hole 422. Furthermore, there is the possibility to use two holes to fill the hollow body 40. One hole possibly on the bottom side of the housing 4 to fill in the fluid and one small hole on top to gather the air bubbles collected in opening 423. In case only hole 422 is used to pump in fluid, it will need tubes on its side drilled in at a certain inclination to have air coming out while pumping in fluid. After fluid has pumped in, the grease nipple will be screwed over holes of the air tubes to seal them. It is also possible to use a system to evacuate the hollow body 40 first and pump in fluid afterwards in one process through one hole.

The vane type piston 50 contains the aperture 502 connecting the fore-chamber 43 and the back-chamber 44. The aperture 502 is configured such that it can be closed by the ball-like gravity controlled means 7 disposed within the back-chamber 44. The aperture 502 is further surrounded by a ring seal 503 in order to assure an effective closing effect.

Furthermore, the vane type piston 50 contains the bypass 504 also connecting the fore-chamber 43 with the back-chamber 44. Said bypass 504 is provided with the valve 8 which is operated by the operating means 81 disposed within the opening 421 of the separating member 42.

FIGS. 8A and 8B show a detailed illustration of the valve 8 in an open and a closed state, respectively.

FIG. 8A shows the ankle in a state, in which no load is on the artificial ankle. In this state, the elastomeric pad 61 between the frame 60 and the pyramid adapter 64 is in a non-deformed state. As a consequence, an elastomeric pad 816 between the separating member 42 of the housing 4 and the operating cap 815 is also not compressed so that the bar magnet 812 connected to the operating cap 815 is arranged at a maximal distance from the valve 8 within the bar magnet duct 813 formed within the separating member 42. In this state, the induction disk 810 is disposed at the bottom of the induction disk duct 811 also formed within the separating member 42 below the bar magnet duct 813 and next to the valve 8. The induction disk 810 is configured such that it is able to lift an iron ball 802 coated with a plastic material as component of the valve 8. The valve 8 disposed within the bypass channel 504 contains said iron ball 802 disposed within a cavity 804, which is boarded at one side by a ring 800 having a conical cross-section, the ring 800 being disposed in front of a ring magnet 803, the ring 800 and the ring magnet 803 as well as a housing 805 of the valve 8 form a flow channel 801. Instead of iron ball 802 a magnetic ball may also be used. The ball 802 has preferably a smaller diameter than the minimal dimension of the cavity 804. In the state shown in FIG. 8A, the ball 802 is lifted by the induction disk 810 so that the ball 802 is removed from the valve seat built by the ring 800 having the conical cross-section so as to open the flow channel 801.

FIG. 8B in contrast shows the artificial ankle 3 in a loaded state. As presented, the elastomeric pad (PU spring pad) 61 is compressed, when the load increases to a force of preferably more than 200 N, so that the pyramid adaptor 64 and the underbody 62 connected to said pyramid adapter 64 are moved relative to the frame 60 and towards the housing 4. This motion causes the operating cap 815 to move downwardly so as to compress the elastomeric pad (PU spring pad) 816. The motion of the operating cap 815 causes the bar magnet 812 connected to the operating cap 815 to move downwardly in the direction of the valve 8 within the bar magnet duct 813. This causes the bar magnet 812 to move towards the induction disk 810, so that said induction disk 810 is attracted by the bar magnet 812 and therewith lifted upward.

As said induction disk 810 is removed by the motion of the bar magnet 812 away from the valve 8 within the piston 50, the attraction of the ball 802 of the valve 8 by the induction disk 810 decreases so that the ball 802 lowers itself and moves towards the valve seat 800 so as to close the flow channel 810. The flow through the bypass 504 causes the ball 802 to last within the valve seat 800 so that the valve 8 is closed as long as the duct magnet 810 is lifted by the bar magnet 812.

After the load on the artificial ankle 3 is removed when the artificial foot 1 is lifted from the ground, the elastomeric pads 816 and 61 decompress and press the operating cap 815 and the pyramid adapter 64 together with the underbody 62 away from the valve 8. The bar magnet 812 together with the operating cap 815 moves upwards away from the induction disk 810, so that said induction disk 810 falls to the bottom of the induction disk duct 811. In this state, the induction disk attracts the ball 802 of the valve 8 and removes said ball 802 from the valve seat 800 so as to free the flow channel 801.

FIGS. 9A to 9C describe an alternative construction of the valve 8 within the bypass 504. The operating mechanism of the valve 8 disposed within the separating member 42 is configured in the identical way as described with respect to FIGS. 8A and 8B.

In FIG. 9A, an exploded view of said alternative valve 8a is presented. A housing 804 has a cylindrical shape and is provided with a flow channel 801 along the rotational axis of said housing 804. At its left and right ends, the housing 804 has grooves for seal rings 805. In the middle part of the housing 804, a recess is formed for an elastomeric spring 806 and a valve stem 807 provided with a throughhole 808 in a direction parallel to the rotational axis of the housing 804. The valve stem 807 is adapted to move within the recess perpendicular to the rotational axis of the housing 804.

FIG. 9B shows the valve 8a in an assembled state. The ring seals 805 are disposed within the grooves of the housing 804 and the elastomeric spring 806 and the valve stem 807 are disposed within the recess of the housing 804.

FIG. 9C presents the valve 8 incorporated within the bypass 504 of the piston 50. In case of no load on the ankle, the induction disk 810 is disposed at the bottom of the induction disk duct 811 within the separating member 42, as shown in FIG. 8A. In this case, the elastomeric spring 806 is compressed by the attraction force between the valve stem 807 and the induction disk 810 and the valve stem 807 is moved upwardly, so that the throughhole 808 in the valve stem 807 is disposed along the rotational axis of the housing 804 so as to free the flow channel 801. In case that the induction disk 810 is lifted by the bar magnet 812 by providing a load to the ankle 3, the attraction force between the induction disk 810 and the valve stem 807 is decreased so that the elastomeric spring 806 pushes the valve stem 807 downwardly, so as to close the flow channel 801. This state is shown in FIG. 9C.

Alternatively, the valve 8a shown in FIG. 9B can be turned around the rotational axis around an angle of 180° and the operating mechanism of the valve 8 is configured without said induction disk 810. In this case, the elastomeric spring 806 is adapted to pull the valve stem 807 downwardly so as to open the flow channel 801 in case of no load.

When the bar magnet 812 within the bar magnet duct 813 in the separating member 42 is pushed down by a load on the ankle 3, said bar magnet 812 attracts the valve stem 807 and strains the elastomeric spring 806 so as to close the flow channel 801.

Returning to FIG. 7, it is demonstrated, that the separating member 42 is formed and disposed such that the angle between the footplate 2 and the attachment means 6 does not extent over a predetermined first angle or below a second predetermined angle. FIG. 7 further shows a cross-section of the attachment means 6 comprising the frame 60 and the pyramid adaptor 64 both being connected to each other by the use of screws 65 and covering the underbody 62 for transferring the load from the attachment means 6 to the valve operating means 81 within the recess 421 through the hole 49 below said underbody 62.

FIGS. 10A to 10C shows the relation of the single components of the rotational piston to each other. In FIG. 10A the side plates 51a, 51b and the plates 532 on the inner side face of the side plates 51a, 51b are connected to each other and the vane-type piston 50 by the pin (not shown). The side plates 51a and 51b have adjacent to their outer side face 511a continuous lateral face 512. Adjacent to the inner side face connected to the seal plates 532a, 532b, a bar 513 along the circumference formed which is provided with a groove 514. The plates 532a, 532b have substantially the same diameter as the side plates 51a, 51b in the region of the bar 513.

In FIG. 10B, the seal rings 531 are disposed around in the grooves 514 of the side plates 51a, 51b. Furthermore, the bar magnet duct 813 is disposed in a vertical direction next to the piston 50. Between the seal plates 532a, 532b the elastomeric return spring 510 is arranges hiding the piston.

In FIG. 10C, the operating cap 815 is shown being in contact with the bar magnet duct 813. Furthermore, the slide bearings 530 cover the continuous lateral face 512 of the side plates 51a, 51b. The slide bearings are formed like a cylinder and have a bar 5301 at its outer edge, that is the edge being in plane with the outer side face 511 of the side plates 51a, 51b.

FIGS. 11A to 11C show the housing 4 of the ankle 3 in detailed views.

FIG. 11A shows a perspective view on a housing 4 cut along a vertical plane along the rotational axis of the housing 4. Within the housing 4, in contact with the cylindrical surface 41 of the housing 4, the separating member 42 is arranged. Said separating member contains the throughhole 420 for the elastomeric return spring 510. Furthermore, the recess for the operating mechanism for the valve 8 is shown, containing the induction disk duct 811 and the bar magnet duct 813 as well as a recess for the operating cap 815.

FIG. 11B shows the front view on the cutting plane in FIG. 11A. Again, the separating member 42 including the recess for the operating mechanism for the valve 8 is shown. FIG. 11B further shows a cutting plane H-H, the cross-sectional view on the housing along said cutting plane H-H is shown in FIG. 11C. Therein, the hollow body built by the inner cylindrical surface 41 of the housing 4 and the separating member 42 is shown. Besides the throughhole 420 and the recess for the operating mechanism for the valve 8, a throughhole 422 configured to charge the hollow body 40 with hydraulic fluid and an opening 423 for buffering a reserve of hydraulic fluid and a gathering placed for air bubbles are shown. Optionally, the fluid can be pumped into the hollow body 40 using a grease gun or a grease nipple which may be screwed in the hole 422.

In FIGS. 12A and 12B, an alternative construction of the supply hole 422 for the hydraulic fluid is shown. As shown in FIG. 12A, the hole 422 in the separating member 42 of the housing 4 is split into a small hole 422a and a hole 422b having a greater diameter, which is provided to fill the hydraulic fluid into the hollow body 40. Within the throughhole 422b, the grease nipple 49 is disposed. In the state of filling in fluid, the grease nipple 49 is arranged above the separation portion 425 in order to open the small hole 422a so as to release air bubbles out of the hollow body 40 and the opening 423. As shown in FIG. 12B, after the fluid has been filled into the hollow body 40, the grease nipple 49 is screwed or pushed into the separating portion 425 so as to close the small hole 422a and the hole 422b.

Figure 13A:
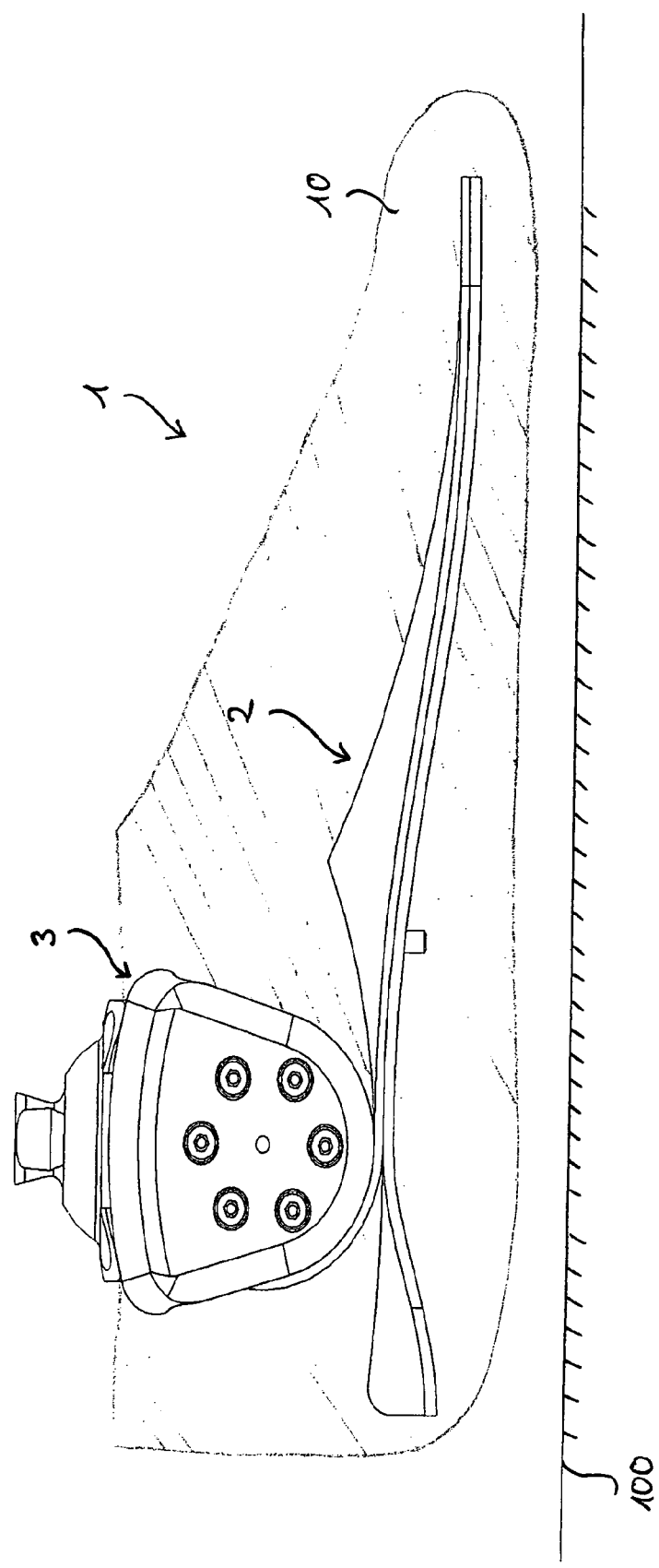

FIGS. 13A to 13E show several perspectives of the artificial foot 1 according to the present invention, wherein the angle 3 between the footplate 2 and the attachment means 6 changes dependent on the inclination of the ground 100. In FIG. 13A, the footplate 2 disposed within the cover 10 is disposed horizontally. The artificial ankle 3 attached to said footplate 2 is in a position, so that the attachment means 6, in particular the pyramid adapter 64, is substantially perpendicular to the sole of the foot 1 and the horizontal ground 100.

Figure 13B:
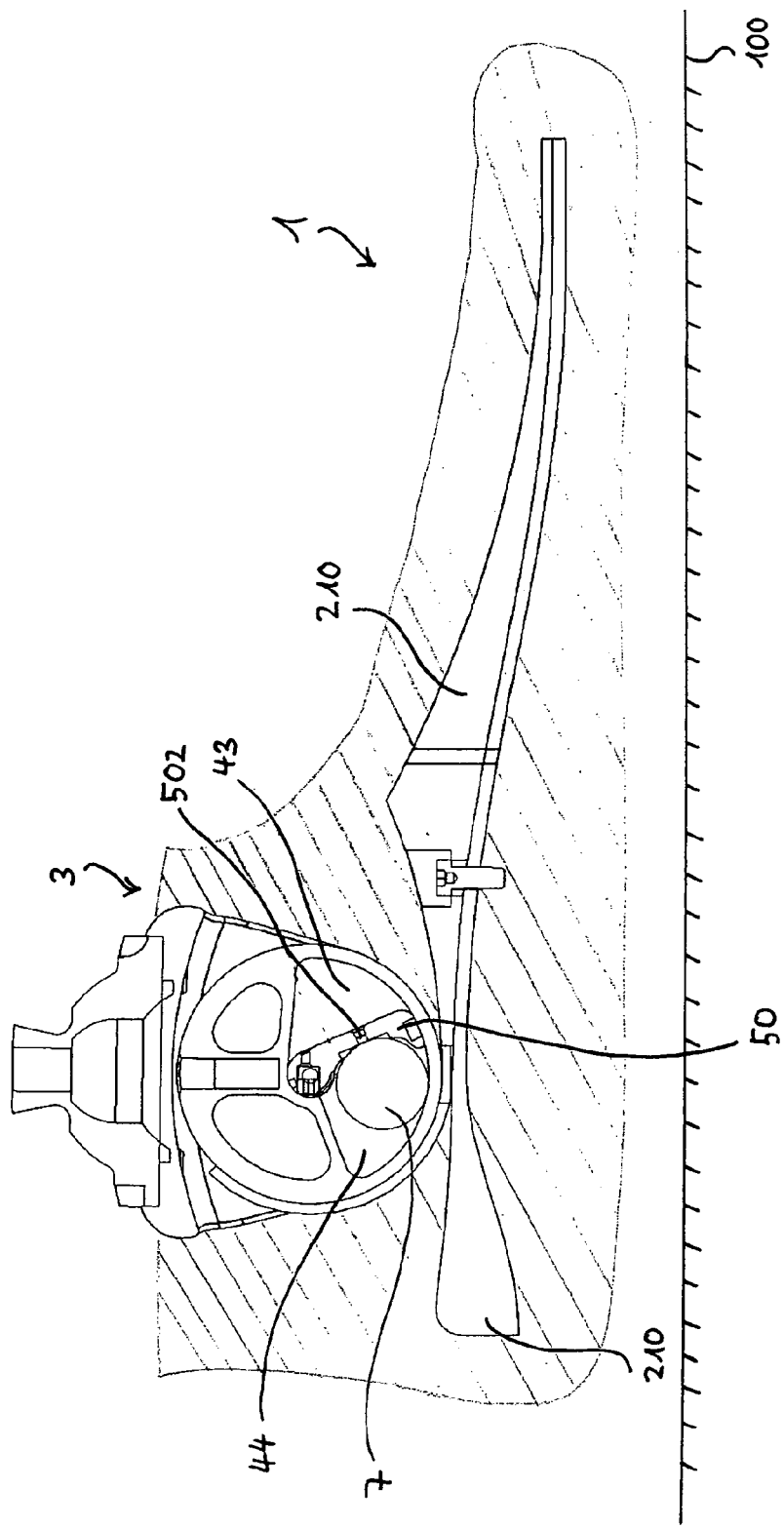
Figure 13C:
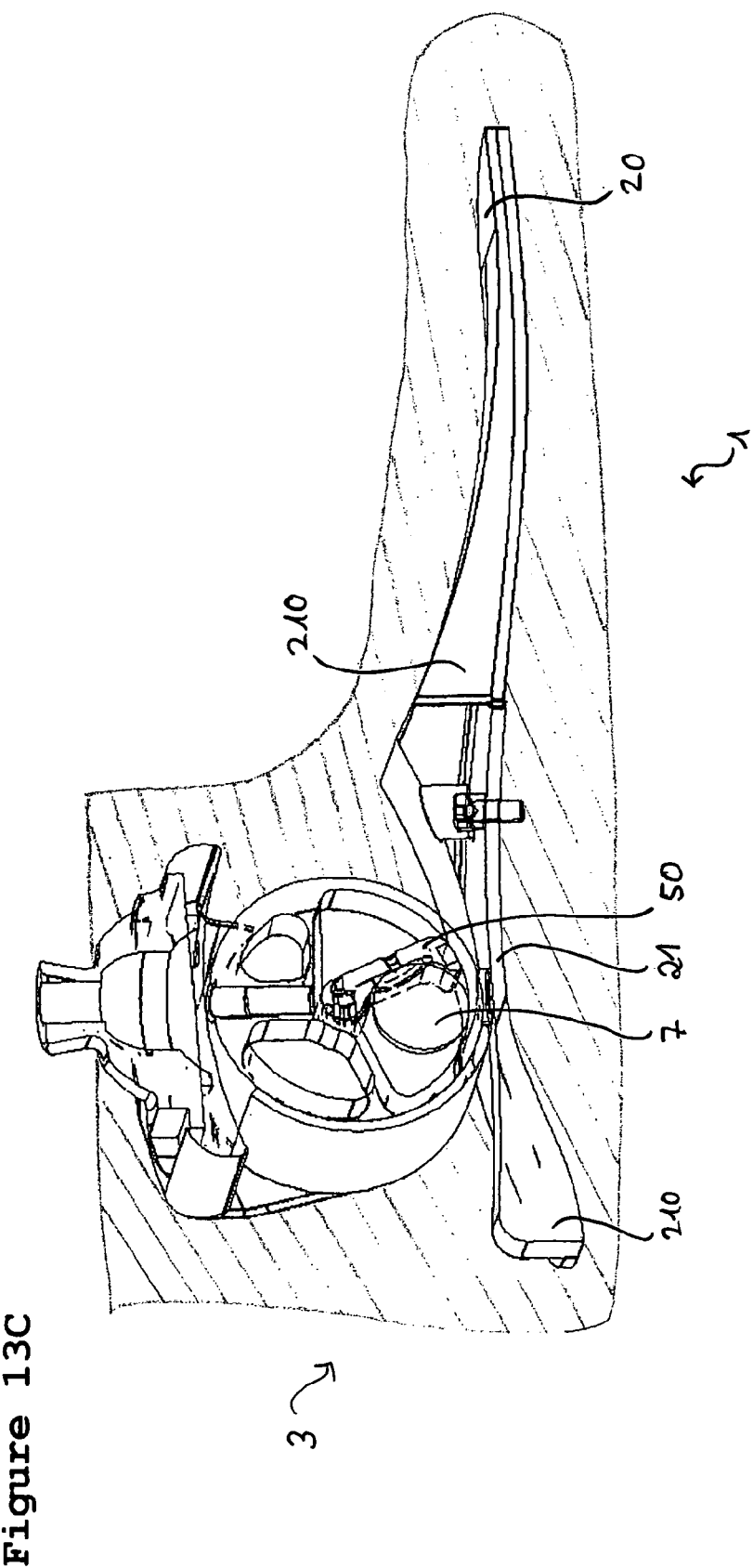

FIG. 13B shows a cross-sectional view of the foot 1 shown in FIG. 13A. The ankle 3 is configured in principle in the same as that described with respect to FIGS. 4, 6A and 6B. The ball 7 in the back-chamber 44 of the hollow body 40 is at the minimal possible position on the cylindrical surface area 41 of the housing and seals the aperture 502 of the piston 50.

FIG. 13C shows again the foot according to FIG. 13A in a cross-sectional perspective view. It is to be noted that in case of FIGS. 13A to 13E, the back-footplate 21 has a reinforcing thickening in the region of the heel 210. Furthermore, the fore-footplate 20 has a thickening or a reinforcement member in the region of the middle foot 201. This thickening or reinforcement member allows bending the footplate until a desired curvature (roll-over shape) and then stops a further deformation. The forced stop of deformation is caused in particular by a massive arrester at the housing.

Figure 13D:
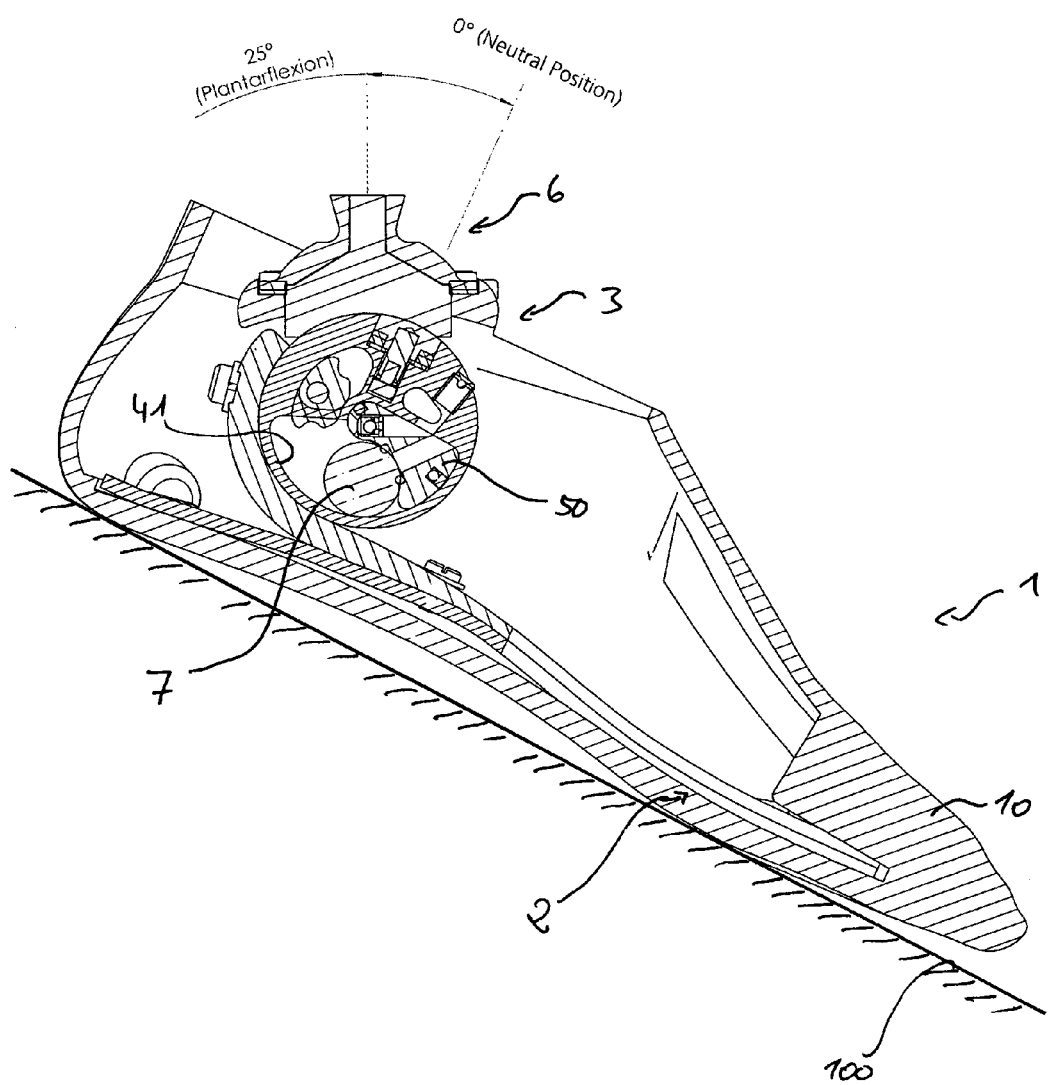

FIG. 13D presents the artificial foot 1 according to the present invention on an inclined ground 100 during a downhill motion, wherein again the foot plate 2 is flat on the ground 100 and the attachment means 6 is in a vertical position. The inclination of the ground 100 corresponds to the maximal possible inclination for walking with the artificial foot 1 downhill. In this case, the ball 7 is at the minimum of the cylindrical surface area 41 and the maximal angle of backward rotation is achieved, as the piston 50 contacts the separating member 42, so that the fore-chamber 43 of the hollow body 40 disappears. A further extension of the angle between the sole of the foot 1 and the attachment means 6 is impossible. In this case, a maximal plantarflexion is achieved.

FIG. 13E presents the artificial foot 1 on an inclined ground 102 during a uphill motion, wherein again the foot plate 2 is flat on the ground 100 and the attachment means 6 is in a vertical position. The inclination of the ground 100 corresponds to the maximal possible inclination for walking with the artificial foot 1 uphill. In this case, the ball 7 is at the minimum of the cylindrical surface area 41 and the maximal angle of forward rotation is achieved, as the piston 50 is blocked by the ball 7, which is pressed against the separating member 42, so that the back-chamber 44 becomes minimal. A further minimization of the angle between the foot sole and the attachment means 6 is therefore not possible and the maximal dorsiflexion is achieved.

Each of FIGS. 14A and 14B show four positions of the artificial foot 1 according to the invention during a gait cycle for uphill movement at an inclination of 20° (FIG. 14A) and a downhill movement at an inclination of 20° (FIG. 14B).

For each position an artificial foot 1 on the inclined ground 100 is shown, wherein the foot 1 is constructed as described above. In the following, the gait cycle of said artificial foot 1 including the positions A to D of FIGS. 14A and 14B is described:

At an initial contact, the heel portion 210 of the back-foot plate 21 touches the ground 100. A deformation of the carbon fiber structures and in some cases, where springs are provided within the artificial ankle 3, a deformation of the springs provide a first initial damping of decelerated body mass of the amputee (position A).

At loading response, the foot 1 is passively flexed until it rests flat on the ground 100. The piston 50 is hence pivoting around the rotational axis. Due to an increase of the body weight, the operating means 81 pushes downward, so the bypass channel 504 is closed. The fluidic resistance of the control channel 502 (diameter) in combination with the preselected viscosity of the hydraulic fluid are hence determining the mechanical characteristics of the foot 1.

At mid stance, a shank to be mounted to the pyramid adapter 64 pivots over the foot 1 forward and hence the piston 50 pivots around the rotational axis, too (position B). The ball 7 has seeked for the lowest point on the convex shaped housing surface 41. When the piston 50 is in a parallel position to the vector of the gravity force, the ball 7 blocks the control channel 502. Hence the ankle joint 3 is blocked.

Until terminal stance, the body weight pivots even further forward. Due to the blocked ankle joint 3, the fore-foot is bended into a circular shape that is terminal restricted by the bottom of the housing 4 or by structures on the fore-foot plate being connected to the fore-foot by an adhesive or by screws (position C). This feature provides better energy storing characteristics of the prosthesis. Due to the compressible characteristics of the hydraulic fluid, the attachment means is pivoting slightly into a dorsiflexed position. The fore-foot is preferably a massive component, in particular made of plastic material.

In pre-swing, the foot 1 is lifted off the ground 100. The deformed fore-foot is flexing back to its initial position providing energy return.

At mid swing, the load on the foot 1 is removed and hence, a spring underneath the pyramid adaptor pushes the device upward allowing the pressure difference between both hydraulic chambers to equalize. Compression springs inside the housing 4 are resetting the foot 1 back to its neutral position. The ball 7 is later on able to roll freely inside the housing. Hence, the prosthetic foot 1 is prepared for the next step.

FIG. 15 shows a further embodiment of the artificial foot 1 according to the present invention in an exploded view. At the bottom of the figure, a back-footplate 21 and a fore-footplate 20, which are to be connected using screws 22 are shown. Above the fore-footplate 20, the housing 4 is shown, a housing 4 having a hollow body 40 with a partially cylindrical inner surface 41 and a further part being defined by a separating member 42 limiting the cross-section of the hollow body to less than a half-circle. The hollow body 40 is limited on one face side of the hollow body by a housing wall 45 having an aperture for the supporting elements 507 of the vane type piston 50. On the left side of the housing 4, the vane type piston 50 is shown. Said vane type piston 50 contains a vane 506 and supporting elements 507. Said vane 506 has projections 508 for neutralizing springs 55 which are to be fixed using screws 550 to the projection 508. To each of the supporting elements 507 a slide bearing 530 is brought to cover the cylindrical surface of said supporting elements 507.

The vane 506 of the vane type piston 50 is provided with a rectangular sealing 509 for sealing chambers 43, 44 built by the vane type piston 50 in the hollow body 40.

In the left of the vane type piston 50, the ball-like gravity controlled means 7 is shown, which is to be disposed together with the vane type piston 50 into the hollow body 40 of the housing 4. As soon as the vane type piston 50, the slide bearings 530, the seals 509, the springs 55 and the ball 7 are disposed correctly within the hollow body 40 of the housing 4, a separate wall 46 having a centrally disposed aperture 460 for the supporting member 507 and having several through holes 461 positioned corresponding to holes 400 in the housing 4 can be fixed to the housing 4 with screws 462.

On the right and left of the components described, a sealing ring 533 with a small diameter and a sealing ring 534 with a bigger diameter as well as a ring-like plate 535 are shown, which are to fluid tight seal the hollow body 40. Furthermore, a pin 52 around which the vane type piston 50 can be turned is used to fix all components of the rotating piston by the use of nuts 54.

The screws 31 are used for fixing the frame 60 of the attachment means 6. Above the housing 4, a valve stem 82 is shown, which is adapted to be arranged within a hole 49 on top of the housing 4, within which a bypass system is formed which is provided with a valve 8 to be operated by said valve stem 81. The attachment means 6 contains besides the frame 60 the pyramid adaptor 64, the screws 65 to connect the pyramid adaptor 64 to the frame 60, a terminal impact bumper 61, an underbody 62 and weight activated bumpers 63 which are disposed between the frame 60 and the pyramid adaptor 64.

The artificial foot 1 of FIG. 15 is shown in FIG. 16 as side view. The housing 4 has the hollow body 40 separated into the fore-chamber 43 and the back-chamber 44, being separated by the vane type piston 50. In the back-chamber 44, the ball-like gravity controlled means 7 is disposed. The vane type piston 50 comprises projections 508 into the fore-chamber 43 and the back-chamber 44, to which the neutralizing springs 55 are connected by the use of screws 550. The vane type piston 50 further provides an aperture 502 allowing the flow of fluid between the fore-chamber 43 and the back-chamber 44. To said aperture 502 on the side orientated towards the back-chamber 44, seals 503 are provided in order to assure that the aperture 502 is closed by the ball-like gravity controlled means 7.

In contrast to the previous embodiment, the embodiments of FIGS. 15 and 16 show a bypass 504 which is formed within the separating member 42 of the housing 4 and which combines the fore-chamber 43 and the back-chamber 44. To said bypass 504, a valve 8 is attached, which is operated by the valve stem 82, upon load to the attachment means 6. In order to operate said valve stem 82 said attachment means 6 are led in a recess 48 which is connected to the recess 421 for the valve 8 including the valve 8.

FIGS. 17A to 17C show an artificial ankle 3a which allows not only dorsiflexion (forward rotation) and plantarflexion (backward rotation), but also allows inversion and reversion, i.e. a combination of rotation around an axis perpendicular to the axis for dorsiflexion and plantarflexion and in longitudinal direction of the foot part. For this purpose, the housing of the ankle is divided into a left housing 4a and a right housing 4b. The left and the right housing 4a, 4b are preferably separated by a plate-like disk so as to provide fluid tight hollow bodies in each of the housings.

The frame 60 of the attachment means is in this example configured as basic portion 600 to which the side portions 601 are attached in a manner so as to allow relative movement. For this purpose, the side portions are provided with guiding openings 602 for guiding pins 603 of the basic portion 600. The other components of the attachment means are configured as explained with respect to the previous examples.

In FIG. 17A, the ankle is in a neutral position, wherein the pins 603 are in the middle of the guiding opening 602. In FIG. 17B, the left side portion 601 is tilted out of the plane of projection and the right side portion is tilted into the plane of projection. This relative rotation of the side portions 601 causes the pins 603 within the guiding opening 602 to move upwards or downward respectively so as to cause the pyramid adapter 64 to rotate in a counterclockwise direction.

FIG. 17C shows the opposite situation to that shown in FIG. 17B. Here, the left side portion 601 is tilted into the plane of projection, while the right side portion 601 is tilted out of said plane. The pins 603 are positioned at the bottom and the top of the openings 602 respectively and the pyramid adapter 64 is turned in a clockwise rotation.

In order to allow such a rotation, a piston 50a and 50b is disposed in each housing 4a and 4b, the pistons 50a, 50b being rotatable relative to each other and being elastically coupled by an elastic coupling 56, as shown in FIG. 18. The two pistons 50a and 50b are both rotatably around the axis 57 as indicated by the arrow 58, wherein the left piston 50a is rotated by an angle $\phi_1$ from a starting position, while the right piston 50b is rotated by an angle $\phi_2$ from said starting position indicated by line 59, wherein $\phi_1 < \phi_2$.

FIG. 19 shows a simplified presentation of the ankle, wherein the housings 4a and 4b are in a starting position. The housings 4a and 4b are presented having a window in the portion of the hollow body 40 so as to show that the piston 50a within the housing 4a has a different inclination than the piston 50b within the housing 4b.

FIG. 20 shows, as already presented by FIG. 17C, that the inclination of the piston 50a is amended by an angle of 5°, while the inclination of the piston 50b is unamended. The relative rotation of the two pistons causes the attachment means to rotate in a clockwise direction as indicated by the arrow 66.

FIG. 21 shows the cross-sectional view of a piston 50, which has a two-way flow control instead of the aperture 502 shown in previous embodiments. The piston 50 has two apertures 5020 and 5021, each provided with a valve 8a, 8b opening in different directions, wherein the lower aperture 5020 has a channel diameter A1 and the upper aperture 5021 has a channel diameter A2, wherein A1≠A2. The lower aperture 5020 is responsible for the flow control for dorsiflexion (bending of the ankle), while the upper aperture is responsible for the flow control for plantarflexion (elongation). Such a configuration allows that a forward direction is performed at a different velocity than the rotation in the opposite direction.

FIG. 22 also shows a piston with an aperture 502 provided with a velocity control 71. Said velocity control generates a turbulent flow through the control channel, which influences the velocity of the flow. The high velocity results from a turbulent flow resulting in a high resistance, while a low velocity is achieved by a laminar flow having a low flow resistance.

Concluding, the present invention provides an artificial ankle, foot and leg, which enable the user to properly walk in any possible environment. The artificial ankle, foot and leg of the present invention are constructed in a simple way and avoid problems concerning leakage of hydraulic fluid.

The invention claimed is:

1. Artificial ankle (3) comprising
   a housing (4) comprising a hollow body (40) for retaining a hydraulic fluid, the hollow body (40) having an inner face, at least a part thereof having a cylindrical surface area (41);
   a vane type piston (50) arranged in the hollow body (40), the vane type piston (50) being pivotable about the rotational axis of said cylindrical surface area (41) in a sealing manner with at least said cylindrical surface thereby separating in a fluid tight manner both sides of the vane type piston (50), and the vane type piston (50) having an aperture (502) to allow fluid to move between both sides of the piston (50);
   at least one gravity controlled means (7) for opening or closing said aperture (502);
   the piston (50) having a supporting element (51a, 51b, 507) at at least one of its axial ends, the supporting element (51a, 51b, 507) being arranged in a fluid tight sealing manner in order to retain said hydraulic fluid within the hollow body (40); and
   attachment means (6) for attaching a shank to the artificial ankle (3), said attaching means (6) being fixed to the at least one supporting element;
   wherein the vane type piston (50) and the gravity controlled means (7) are configured to close said aperture (502), when the attachment means (6) is in a position so as to fix a shank in a substantially vertical position; and
   the hollow body (40) comprises a separating member (42) configured to separate the inner volume of the hollow body (40) in two separate partial volumes (43, 44), the partial volumes being separated from each other in a fluid tight manner, the partial volumes (43, 44) being bordered each by one side of the vane type piston (50).

2. Artificial ankle (3) according to claim 1, characterized in that at least one of said gravity controlled means (7) has a cylindrical or spherical surface for freely rolling on the cylindrical surface area (41) of the hollow body (40) on one side of the vane type piston (50).

3. Artificial ankle (3) according to claim 1, characterized in that the housing (4) and/or the vane-type piston (50) are provided with
- a bypass channel (504) for the hydraulic fluid connecting both partial volumes (43, 44) on both sides of the vane type piston (50),
- a valve (8) for opening or closing the bypass channel (504) operated by an operating member (81, 82) for closing said valve (8) upon a predetermined load to the attachment means (6) arranged at least in the housing.

4. Artificial ankle (3) according to claim 3, characterized in that the attachment means (6) upon load is movable toward a valve stem (82) as valve operating member, thereby pressing the valve stem (82) in a valve seat.

5. Artificial ankle (3) according to claim 1, characterized by means for limiting forward rotation of the vane type piston (50) from a neutral position with no load to the attachment means, in particular to 30°, in particular 20°, in particular 15° and/or for limiting backward rotation of the vane type piston (50) from a neutral position with no load to the attachment means, in particular to 90°, in particular to 30°, in particular to 20°, in particular to 15°.

6. Artificial ankle (3) according to claim 1, characterized by a fluid tight ring seal (531) between the supporting element (51a, 51b, 507) of the piston (50) and the housing (4).

7. Artificial foot (1) comprising a foot plate (2) and an ankle (3) according to claim 1, wherein the foot plate (2) is attached to the housing (4) of the ankle (3).

8. Artificial foot (1) according to claim 7, characterized by means to adjust the relative position of the housing (4) of the ankle (3) and the footplate (2).

9. Artificial foot (1) according to claim 8 wherein said means to adjust comprises an adjustment screw (25) seated in the ankle (3) or the footplate (2) and acting on the footplate (2) or ankle (3) respectively.

10. Artificial ankle (3) comprising
- a housing (4) comprising a hollow body (40) for retaining a hydraulic fluid, the hollow body (40) having an inner face, at least a part thereof having a cylindrical surface area (41);
- a vane type piston (50) arranged in the hollow body (40), the vane type piston (50) being pivotable about the rotational axis of said cylindrical surface area (41) in a sealing manner with at least said cylindrical surface thereby separating in a fluid tight manner both sides of the vane type piston (50), and the vane type piston (50) having an aperture (502) to allow fluid to move between both sides of the piston (50);
- at least one gravity controlled means (7) for opening or closing said aperture (502);
- the piston (50) having a supporting element (51a, 51b, 507) at at least one of its axial ends, the supporting element (51a, 51b, 507) being arranged in a fluid tight sealing manner in order to retain said hydraulic fluid within the hollow body (40); and
- attachment means (6) for attaching a shank to the artificial ankle (3), said attaching means (6) being fixed to the at least one supporting element;
- wherein the vane type piston (50) and the gravity controlled means (7) are configured to close said aperture (502), when the attachment means (6) is in a position so as to fix a shank in a substantially vertical position;
- wherein the housing (4) and/or the vane-type piston (50) are provided with
- a bypass channel (504) for the hydraulic fluid connecting both partial volumes (43, 44) on both sides of the vane type piston (50),
- a valve (8) for opening or closing the bypass channel (504) operated by an operating member (81, 82) for closing said valve (8) upon a predetermined load to the attachment means (6) arranged at least in the housing; and
- the bypass channel (504) and the valve (8) are arranged within the vane type piston (50).

11. Artificial ankle (3) comprising
- a housing (4) comprising a hollow body (40) for retaining a hydraulic fluid, the hollow body (40) having an inner face, at least a part thereof having a cylindrical surface area (41);
- a vane type piston (50) arranged in the hollow body (40), the vane type piston (50) being pivotable about the rotational axis of said cylindrical surface area (41) in a sealing manner with at least said cylindrical surface thereby separating in a fluid tight manner both sides of the vane type piston (50), and the vane type piston (50) having an aperture (502) to allow fluid to move between both sides of the piston (50);
- at least one gravity controlled means (7) for opening or closing said aperture (502);
- the piston (50) having a supporting element (51a, 51b, 507) at at least one of its axial ends, the supporting element (51a, 51b, 507) being arranged in a fluid tight sealing manner in order to retain said hydraulic fluid within the hollow body (40); and
- attachment means (6) for attaching a shank to the artificial ankle (3), said attaching means (6) being fixed to the at least one supporting element;
- wherein the vane type piston (50) and the gravity controlled means (7) are configured to close said aperture (502), when the attachment means (6) is in a position so as to fix a shank in a substantially vertical position;
- wherein the housing (4) and/or the vane-type piston (50) are provided with
- a bypass channel (504) for the hydraulic fluid connecting both partial volumes (43, 44) on both sides of the vane type piston (50),
- a valve (8) for opening or closing the bypass channel (504) operated by an operating member (81, 82) for closing said valve (8) upon a predetermined load to the attachment means (6) arranged at least in the housing; and
- the attachment means (6) upon load is movable toward a magnetic coupling mechanism as the valve operating member (81), thereby moving a magnetic element in a valve seat.

12. Artificial ankle (3) comprising
- a housing (4) comprising a hollow body (40) for retaining a hydraulic fluid, the hollow body (40) having an inner face, at least a part thereof having a cylindrical surface area (41);
- a vane type piston (50) arranged in the hollow body (40), the vane type piston (50) being pivotable about the rotational axis of said cylindrical surface area (41) in a sealing manner with at least said cylindrical surface thereby separating in a fluid tight manner both sides of the vane type piston (50), and the vane type piston (50) having an aperture (502) to allow fluid to move between both sides of the piston (50);
- at least one gravity controlled means (7) for opening or closing said aperture (502);
- the piston (50) having a supporting element (51a, 51b, 507) at at least one of its axial ends, the supporting element (51a, 51b, 507) being arranged in a fluid tight sealing manner in order to retain said hydraulic fluid within the hollow body (40); and attachment means (6) for attaching a shank to the artificial ankle (3), said attaching means (6) being fixed to the at least one supporting element, the attachment means (6) including a fork with a joint (600) and two arms (601), one arm being fixed to each supporting element (51*a*, 51*b*, 507) of the vane type piston (50); and wherein the vane type piston (50) and the gravity controlled means (7) are configured to close said aperture (502), when the attachment means (6) is in a position so as to fix a shank in a substantially vertical position.

13. Artificial leg comprising an artificial foot (1) according to claim 12 and a shank, wherein the shank is attached to the attachment means (6) in substantially straight alignment with the rotational axis.

\* \* \* \* \*